(12) United States Patent
Kameda

(10) Patent No.: US 7,174,335 B2
(45) Date of Patent: Feb. 6, 2007

(54) MEDICAL INFORMATION SYSTEM AND COMPUTER PROGRAM PRODUCT

(75) Inventor: Toshitada Kameda, Tokyo (JP)

(73) Assignee: Kameda Medical Information Laboratory, Tokyo (JP)

( * ) Notice: Subject to any disclaimer, the term of this patent is extended or adjusted under 35 U.S.C. 154(b) by 507 days.

(21) Appl. No.: 10/793,864

(22) Filed: Mar. 8, 2004

(65) Prior Publication Data

US 2005/0049897 A1 Mar. 3, 2005

(30) Foreign Application Priority Data

Aug. 28, 2003 (JP) ............... 2003-305153

(51) Int. Cl.
*G06F 7/00* (2006.01)
(52) U.S. Cl. ............... 707/10; 707/5; 707/102; 707/103 X; 707/201
(58) Field of Classification Search ............... 707/10
See application file for complete search history.

(56) References Cited

U.S. PATENT DOCUMENTS

| 2002/0194131 | A1* | 12/2002 | Dick ............... 705/51 |
| 2003/0004756 | A1* | 1/2003 | Okamoto et al. ............... 705/2 |
| 2003/0236683 | A1* | 12/2003 | Henderson et al. ............... 705/2 |
| 2004/0059603 | A1* | 3/2004 | Brown et al. ............... 705/2 |
| 2004/0083123 | A1* | 4/2004 | Kim et al. ............... 705/2 |
| 2005/0065817 | A1* | 3/2005 | Mihai et al. ............... 705/2 |
| 2005/0159986 | A1* | 7/2005 | Breeland et al. ............... 705/3 |
| 2006/0020622 | A1* | 1/2006 | Shelton ............... 707/102 |

FOREIGN PATENT DOCUMENTS

| JP | 06-314288 | 11/1994 |
| JP | 08-272861 | 10/1996 |
| JP | 09-135816 | 5/1997 |
| JP | 10-049608 | 2/1998 |
| JP | 11-312201 | 11/1999 |
| JP | 11-338950 | 12/1999 |
| JP | 2001-297153 | 10/2001 |
| JP | 2002-032478 | 1/2002 |
| JP | 2002-117142 | 4/2002 |
| JP | 2002-215797 | 8/2002 |
| JP | 2003-162586 | 6/2003 |

* cited by examiner

*Primary Examiner*—Don Wong
*Assistant Examiner*—Binh Van Ho
(74) *Attorney, Agent, or Firm*—Young & Thompson

(57) ABSTRACT

A medical information system is provided with: a medical server apparatus for providing an electronic chart for a plurality of the medical terminals for each medical-related facility; a patient server apparatus; a shared server apparatus; a plurality of medical terminals, and a patient terminal, which are included in a communication network. The patient server apparatus provides a patient participatory chart for the patient terminal in case that one patient agrees about medical announcement on the basis of announcement agreement information. The shared server apparatus provides a shared chart for at least one of the plurality of medical terminals in case that the one patient agrees about the provision on the basis of provision agreement information.

22 Claims, 13 Drawing Sheets

MEDICAL INFORMATION SYSTEM AND COMPUTER PROGRAM PRODUCT

BACKGROUND OF THE INVENTION

1. Field of the Invention

The present invention relates to a medical information system for managing electronic clinical charts or electronic medical records on a server apparatus and for providing the electronic charts for medical terminals placed at medical-related facilities, such as hospitals, and for a patient terminal placed at a patient's home.

2. Description of the Related Art

This type of medical information system enables the construction of a network for connecting computers placed at various medical institutions, such as hospitals and clinics. The medical information system also enables the computerization and sharing of medical care information at the medical institutions and enables the mutual reference to the information, by using the computers individually placed at the medical institutions (e.g. refer to Japanese Patent Application Laying Open NO. 2002-117142).

This type of the medical information system also provides medical care information for patients, if the patients apply for it. The application is performed by patients submitting documents which indicate their intention, by patients themselves directly asking doctors for the application during examinations, or the like. Nowadays, many patients desire for the provision of medical care information.

In the above-described medical information system, however, less patients actually use the system than patients who desire to apply for the provision of medical care information because it is hard for the patients to ask doctors for the reason of mental hesitation, or because procedures with the document submission are troublesome, or for the similar reasons. Moreover, considering the fact that patients have difficulty in understanding their medical care information only from doctors' explanation during examinations, it can be said that the above-described medical information system insufficiently discloses the medical care information to the patients. In particular, in the medical information system in which patients can refer to electronic charts or in which electronic charts can be shared at a plurality of medical institutions, there is a risk that a patient who does not desire for medical announcement sees his electronic chart and thus he substantially receives the medical announcement. As described above, there has not been realized a technique which allows for consistency with such medical announcement problems, which allows for guarantee of the right of patients who have the right to use and browse electronic charts and the right to grant the use and browsing, and further which allows for the protection of patient privacy. In addition, if a patient who is not used to refer to electronic charts is allowed to refer to the electronic charts, that may rather cause conflict and massive confusion between the medical-related facilities and the patient because of his anxiety and misunderstanding or the like. Even by using latest communication techniques, such as the Internet, and latest computer techniques, it is extremely difficult, from a technical viewpoint, to let patients smoothly refer to and make electronic charts while these problems are solved at a time, i.e. the problems such as the medical announcement, the guarantee of the rights, and the privacy protection. Moreover, it is more difficult, from a technical viewpoint, to increase the quality of electronic charts, which can be shared at a plurality of medical-related facilities, with the participation of patients and to eventually increase the quality of local medication as a whole while the above problems are solved at a time.

SUMMARY OF THE INVENTION

It is therefore an object of the present invention to provide a medical information system and a computer program product, which can improve the quality of medication through patient participatory medication by using a communication network.

The above object of the present invention can be achieved by a first medical information system provided with: a medical server apparatus for providing an electronic chart, which includes patient data related to medical care of one patient made or obtained through each of a plurality of medical terminals placed at a plurality of medical-related facilities in one local area, for the plurality of the medical terminals for each of the medical-related facilities; a patient server apparatus capable of providing a patient participatory chart, which at least partially includes the electronic chart provided from the medical server apparatus and which includes patient data related to predetermined items made or obtained through a patient terminal operated by the one patient, for the patient terminal; and a shared server apparatus capable of providing a shared chart, which at least partially includes the electronic chart provided from the medical server apparatus and the patient participatory chart provided from the patient server apparatus and which is integrally made for the one patient, for at least one of the plurality of medical terminals, wherein the medical server apparatus, the patient server apparatus, the shared server apparatus, the plurality of medical terminals, and the patient terminal are included in a communication network, at least one of the plurality of medical terminals and the patient terminal is capable of inputting (i) announcement agreement information indicating agreement of the one patient about medical announcement and (ii) provision agreement information indicating agreement of the one patient about provision of the shared chart, and is capable of transmitting at least one of the inputted announcement agreement information and provision agreement information through the communication network, the patient server apparatus (i) provides the patient participatory chart for the patient terminal in case that the one patient agrees about the medical announcement and (ii) does not provide the patient participatory chart for the patient terminal in case that the one patient disagrees about the medical announcement, on the basis of the announcement agreement information transmitted through the communication network, and the shared server apparatus (i) provides, in case that the one patient agrees about the provision on the basis of the provision agreement information transmitted through the communication network: (i-a) the shared chart, which includes the patient data inputted through the patient terminal so as to be one portion of the patient participatory chart for at least one of the plurality of medical terminals if the one patient agrees about the medical announcement; and (i-b) the shared chart not-including the patient data inputted through the patient terminal so as to be one portion of the patient participatory chart for at least one of the plurality of medical terminals if the one patient disagrees about the medical announcement, and (ii) does not provide the shared chart for any of the plurality of medical terminals in case that the one patient disagrees about the provision, on the basis of the provision agreement information transmitted through the communication network.

According to the first medical information system of the present invention, the medical terminals, such as personal computers and workstations, are individually placed at the plurality of medical-related facilities, such as a core hospital (e.g. a large-scaled hospital representing a local area and generally superior in the scale of providing medical care, quality thereof, or the like), a general hospital (e.g. a small-scaled hospital inferior to the core medical-related facility in the scale of providing medical care, quality thereof, or the like), and a clinic, in "one area" or "one local area", such as one administrative district (e.g. one municipality, one prefecture, or the like), one country, and one continent. On the other hand, the patient terminal, such as a personal computer, a mobile, and a mobile phone, is placed at a patient's home or is carried by a patient. Then, these medical terminals and the patient terminal are included in the communication network, such as the Internet and an intranet, together with the medical server apparatus, the patient server apparatus, and the shared server apparatus.

The medical server apparatus provides the electronic chart, which includes the patient data made or obtained through each of the plurality of medical terminals, for the plurality of the medical terminals for each of the medical-related facilities. Namely, each medical-related facility can make the medical server apparatus manage and maintain the electronic chart, which is used at its own facility, through the communication network. Incidentally, the medical server apparatus may be separated into two or more apparatuses depending on the amount of information in the electronic chart which is provided; e.g., an apparatus with relatively high processing power for the core hospital and an apparatus with relatively low processing power for the general hospital or the clinic, or the like. Namely, a plurality of medical server apparatuses included in the communication network may exist for the plurality of medical-related facilities placed in one area.

The patient server apparatus can provide the patient participatory chart, which at least partially includes the electronic chart of this type and which includes patient data related to predetermined items made or obtained through the patient terminal, for the patient terminal. The "predetermined items" are as follows: "a record of a patient's questions and concerns" for a patient recording his questions or worries about medical care; "a patient self-supervision record" for a patient recording his own health care situation (e.g. a medical condition record, a one's medical condition diary, daily vital information and course); "an evaluation record" for a patient recording the evaluation of details of medical care; and "a request record" for a patient recording requests about medicines or treatment. These items make clear questions, worries, and concerns about both medical care and treatment from a patient's viewpoint, some requests to the doctor side, or the like, on the patient participatory chart, with the patient himself as a data supply source.

The shared server apparatus can provide the shared chart, which at least partially includes the electronic chart provided from the medical server apparatus and the patient participatory chart provided from the patient server apparatus and which is integrally or monogenetically made for each patient, for at least one of the plurality of medical terminals. In particular, the shared chart includes even the electronic chart or the patient data made or obtained at other medical-related facilities, so that the shared chart extremely helps improve the quality of medical care at each medical-related facility. Moreover, the shared chart also includes the patient participatory chart made with a patient's participation as described above, so that the shared chart helps improve more the quality of medical care at each medical-related facility.

As described above, the presence of the patient participatory chart and that of the shared chart which may integrally or monogetically include the content of the patient participatory chart, in addition to the electronic chart, gives various benefits to both a patient and the medical-related facilities. Namely, the patient himself can try to promote his health and improve living conditions, and can easily get information even in emergency medical care and in the night. Even if the patient forgets about some patient data, any problems do not occur. Moreover, it is possible to avoid overlapping examinations, overlapping medications, contraindicated medications, or the like. Furthermore, it is possible to improve the quality of medical care by the feedback of the patient's evaluation (i.e. the construction of so-called Plan-Do-Check-Action (PDCA) cycle). These benefits lead to the prevention of internal concealment and the decrease in the number of litigation cases. In addition, it is possible to obtain various practical benefits as follows: easy explanation to a family; possible confirmation of a child by his or her parents; possible confirmation of an elderly person living at a distant place by his son or daughter.

However, only for the reason of convenience, if the patient is allowed to simply participate to make a chart, i.e. to make the patient participatory chart, and to refer to the patient participatory chart, the patient might know his illness and health conditions while making and referring to the patient participatory chart, regardless of whether or not to desire for medical announcement. Namely, it might become the same situation that the medical announcement is substantially made. Therefore, this is a big problem when the patient does not desire for the medical announcement. On the other hand, because it is considered that a patient has the right to browse or use the electronic chart made at each medical-related facility or the right to license the browsing and use, there is a requirement for a technique in which these inherent rights to the patient are supposed to be respected. In addition, only for the reason of convenience, if the shared chart is made simply by a third-party institution except the patient, this may cause the lack of patient privacy protection because the patient data that the patient does not want anyone to know or see, such as patient data at a maternity clinic, is distributed as one portion of the shared chart, while the patient data unuseful at other medical-related facilities is also distributed.

Therefore, according to the first medical information system of the present invention, at least one of the plurality of medical terminals and the patient terminal is capable of inputting and transmitting the announcement agreement information and the provision agreement information. The "announcement agreement information" is inputted as a positive answer to a question, "Do you agree about medical announcement?", for example, and indicates the agreement of each patient about the medical announcement on his own will. On the other hand, the "provision agreement information" is inputted as a positive answer to a question, "Do you agree about the provision of a shared chart?", for example, and indicates the agreement of each patient about the provision of the shared chart on his own will.

On the patient server apparatus side, the patient participatory chart is made on the basis of the announcement agreement information, which is inputted at the patient terminal and the medical terminals in the above manner and which is transmitted to the communication network, under the condition that the patient agrees about the announcement. Then, this patient participatory chart is provided for the patient terminal, and the chart is allowed to referred and recorded by the patient on the patient terminal side, or the like. For example, the patient server apparatus uses its access control function and thereby can control the participation or nonparticipation to the making of the patient participatory chart, or the reference or unreference thereof, for each patient. Therefore, on the patient terminal side, the patient participatory chart can be referred under the condition that the patient himself agrees about the announcement. In this case, there is not much risk of referring to the patient participatory chart by accident and learning own medical conditions or the like although the medical announcement is undesired. Thus, the patient's right to browse and right to refer are respected while the medical announcement problem is solved. Moreover, the patient's participation to the making of the chart allows the making of the patient participatory chart whose quality is expected to improve more. In particular, the patient can receive the patient participatory chart on line from anywhere if the patient is in the environment that the patient can use the communication network. At the same time, the patient can also write information or the like on the chart any time. Therefore, it is possible to decrease the possibility that the patient forgets to record medically important matters.

In the meanwhile, on the shared server apparatus side, the content written by the patient himself of the patient participatory chart, which is made with the patient's participation, is incorporated into the monogenetic or integrative shared chart on the basis of the provision agreement information, which is inputted at the patient terminal and the medical terminals in the above manner and which is transmitted to the communication network, under the condition that the patient agrees about the provision. For example, the shared server apparatus uses its access control function and thereby can control the making or unmaking of the shared chart, or the provision or non-provision thereof, for each patient on the basis of the provision agreement information. Therefore, the electronic chart of the patient of interest can be used as one portion of the shared chart, including the content recorded by the patient himself, not only at the core hospital which mainly makes the electronic chart, but also at a medical-related institution (e.g. a general hospital and a clinic that the patient will go to next) which makes only one portion of the patient's electronic chart or which does not make it at all. Consequently, it is possible to perform the subsequent medical care, treatment, and further its analysis, by maximizing the patient data written by the patient himself and by taking advantage of the shared chart, while the medical announcement problem is solved in the whole local area or community.

As described above, according to the first medical information system of the present invention, it enables the patient to selectively make and refer to the patient participatory chart, and it enables the plurality of medical-related facilities to selectively use the shared chart, which is monogenetic or integrative and which may include the content of the patient participatory chart. Therefore, it is possible to improve the quality of local medication drastically. At the same time, even from the patient's viewpoint, it is possible to maximize the charts to help his own medical and health promotion.

In one aspect of the first medical information system of the present invention, the medical server apparatus (i) provides the electronic chart, which is about the one patient made or obtained on the medical server apparatus for the shared server apparatus in case that the one patient agrees about the provision and (ii) does not provide the electronic chart, which is about the one patient made or obtained on the medical server apparatus, for said shared server apparatus in case that the one patient disagrees about the provision, on the basis of the provision agreement information, and the shared server apparatus at least partially incorporates the electronic chart provided from the medical server apparatus to thereby make the shared chart.

According to this aspect, the provision or non-provision of the electronic chart for the shared server apparatus is controlled on each medical server apparatus on the basis of the provision agreement information received through the communication network. Namely, the making of the shared chart is stopped before the shared server apparatus obtains the patient data. As a result, as long as the patient agrees about the provision, the shared chart can be made safely and surely.

Alternatively, in another aspect of the first medical information system of the present invention, the medical server apparatus provides the electronic chart, which is about the one patient made or obtained on the medical server apparatus for the shared server apparatus, and the shared apparatus (i) at least partially incorporates the electronic chart provided from the medical server apparatus to thereby make the shared chart in case that the one patient agrees about the provision and (ii) does not make the shared chart when the one patient disagrees about the provision, on the basis of the provision agreement information.

According to this aspect, the making or unmaking of the shared chart is controlled on the shared server apparatus on the basis of the provision agreement information received through the communication network. Namely, the making of the shared chart is stopped after the shared server apparatus obtains the patient data. As a result, as long as the patient agrees about the provision, the shared chart can be made safely and surely.

In another aspect of the first medical information system of the present invention, the patient terminal can transmit, through the communication network, chart request information indicating a request for the provision of the patient participatory chart as well as patient identification information indicating identification of the one patient and a password corresponding to the patient identification information, and the patient server apparatus provides the patient participatory chart for the patient terminal in case that the one patient agrees about the medical announcement and that the one patient can be identified by verifying the patient identification information and password transmitted through the communication network.

According to this aspect, the chart request information is transmitted from the patient terminal to the patient server apparatus, with the patient identification information and the password (e.g. an encryption key). Then, the patient server apparatus provides the patient participatory chart for the patient terminal when the patient can be identified by verifying the patient identification information and the password. Therefore, it is possible to prevent effectively that a third person, e.g. a person who pretends to be the patient, improperly refers to the patient participatory chart and further records thereon false information. Namely, it is possible to prevent the improper alternation of the patient participatory chart and that of the shared chart reflecting the patient participatory chart. It is also possible to keep patient privacy protection according to circumstances.

In another aspect of the first medical information system of the present invention, the patient terminal is capable of inputting or changing and transmitting the provision agreement information as well as patient identification information indicating identification of the one patient and a password corresponding to the patient identification information, and the shared server apparatus takes the inputted or changed provision agreement information to be valid in case that the one patient can be identified by verifying the patient identification information and password transmitted through the communication network.

According to this aspect, the provision agreement information is transmitted from the patient terminal to the shared server apparatus, with the patient identification information and the password (e.g. an encryption key). Then, the shared server apparatus takes the provision agreement information to be valid when the patient can be identified by verifying the patient identification information and the password, and performs the subsequent making and provision of the shared chart. Therefore, it is possible to prevent effectively that a third person, e.g. a person who pretends to be the patient, improperly urges the making and provision of the shared chart and improperly refers to this chart. This makes it possible to keep absolute patient privacy protection while highlighting the merits of the shared chart.

In another aspect of the first medical information system of the present invention, the patient terminal is capable of referring to history information indicating a history of use of the patient participatory chart on the patient participatory chart, and each of the medical terminals is not capable of referring to the history information on the electronic chart or the shared chart.

According to this aspect, the history information can be referred by the patient terminal on the patient participatory chart on the patient side. On the other hand, the history of the use of this type cannot be referred by the medical terminals on the medical-related facility side. Therefore, it is absolutely possible to guarantee even the right to know the patient data regarding the patient himself, the right to know the history of the use of the electronic chart, the patient participatory chart, or the shared chart, or the right to keep the history of the use from a third person, all of which are owned on the patient side.

In another aspect of the first medical information system of the present invention, the provision agreement information includes selection information indicating a medical terminal or terminals selected to have the application of the shared chart out of the plurality of medical terminals, the shared server apparatus makes the shared chart so as to at least partially include the electronic chart provided from the medical terminal or terminals selected to have the application of the shared chart and so as not to include the electronic chart provided from a medical terminal regarded not to have the application of the shared chart, on the basis of the selection information, and the shared server apparatus provides the made shared chart for the medical terminal or terminals selected to have the application of the shared chart and does not provide the made shared chart for the medical terminal regarded not to have the application of the shared chart, on the basis of the selection information.

According to this aspect, by virtue of the selection information included in the provision agreement information, the patient can agree about the provision of the shared chart, not for all medical-related facilities without exception, but for each medical-related facility. For example, a medical-related facility which makes the electronic chart including the patient data that the patient does not want anyone to know or see, such as patient data at a maternity clinic, is excepted. Then, the shared chart can be made from the electronic chart made by another medical-related facility and can be provided for the another medical-related facility.

Alternatively, in another aspect of the first medical information system of the present invention, the provision agreement information includes first selection information indicating a medical terminal or terminals selected to have application as a patient data source of the shared chart out of the plurality of medical terminals and second selection information indicating a medical terminal or terminals selected to have application as a providing destination of the shared chart, the shared server apparatus makes the shared chart so as to at least partially include the electronic chart provided from the medical terminal or terminals selected to have the application as the patient data source of the shared chart and so as not to include the electronic chart provided from a medical terminal regarded not to have the application as the patient data source of the shared chart, on the basis of the first selection information, and the shared server apparatus provides the made shared chart for the medical terminal or terminals selected to have the application as the providing destination of the shared chart and does not provide the made shared chart for a medical terminal regarded not to have the application as the providing destination of the shared chart, on the basis of the second selection information.

According to this aspect, by virtue of the first selection information included in the provision agreement information, the patient can agree about a role as the patient data source of the shared chart, not for all medical-related facilities without exception, but for each medical-related facility. Moreover, by virtue of the second selection information included in the provision agreement information, the patient can agree about a role as the providing destination of the shared chart, not for all medical-related facilities without exception, but for each medical-related facility. For example, this aspect is as follows. A medical-related facility which makes the electronic chart including the patient data that the patient does not want anyone to know or see, such as patient data at a maternity clinic, is excepted from the patient data source. Then, the shared chart is made from the electronic chart made by another medical-related facility. The made shared chart is provided for medical-related facilities including the medical-related facility excepted from the patient data source described above. Alternatively, this aspect is as follows. A medical-related facility which is undesired to be excepted from the patient data source, but which is desired to be excepted from the providing destination, e.g. a hospital the patient does not desire for a repeat consultation or the like, is not excepted from the patient data source. Then, the shared chart is made from the electronic chart made by medical-related facilities including the above-described medical-related facility. A medical-related facility which is desired to be excepted from the providing destination is actually excepted from the providing destination. Then, the shared chart is provided for other medical-related facilities.

In another aspect of the first medical information system of the present invention, the medical server apparatus and the shared server apparatus at least partially provide the electronic chart and the shared chart for the patient terminal, the patient terminal is capable of at least partially referring to the electronic chart provided from the medical server apparatus and the shared chart provided from the shared server apparatus in a predetermined format, from a display screen of the patient participatory chart, and is capable of inputting or changing at least one of the provision agreement information and the announcement agreement information, shortly before or after, or at the same time of the display of a reference screen in the predetermined format, the shared server apparatus maintains the inputted or changed provision agreement information, and makes and provides the shared chart in accordance with the provided provision agreement information, and the patient server apparatus maintains the inputted or changed announcement agreement information, and makes and provides the patient participatory chart in accordance with the provided announcement agreement information.

According to this aspect, the electronic chart and the shared chart are at least partially referred on the reference screen in the predetermined format from the display screen of the patient participatory chart on the patient terminal side. Then, shortly before or after, or at the same time of the display of this reference screen, at least one of the provision agreement information and the announcement agreement information is inputted or changed. Then, after confirming the content of the electronic chart and that of the shared chart made by the present time point, the patient can perform input operation indicating the agreement about the provision of the shared chart and the agreement about the medical announcement. For example, after checking the actual content of the electronic chart and after confirming whether or not to provide it as the shared chart, the patient can input or change the provision agreement information. Incidentally, the "change" related to the provision agreement information and the announcement agreement information in the present invention means the change from agreement to disagreement or vice versa.

The provision agreement information inputted or changed after the confirmation in this manner is maintained by the shared server apparatus. Then, the shared chart is made and provided in accordance with this maintained provision agreement information. On the other hand, the announcement agreement information inputted or changed after the confirmation in this manner is maintained by the patient server apparatus. Then, the patient participatory chart is made and provided in accordance with this maintained provision agreement information.

This aspect may be constructed such that the patient terminal can display first mark information indicating to call up the reference screen in the predetermined format on the display screen of the patient participatory chart, and can display the reference screen in the predetermined format by specifying the displayed first mark information.

By constituting in this manner, it is possible to easily refer to one portion of the electronic chart and the shared chart by specifying the first mark information displayed on the display screen of the patient participatory chart. This makes it possible to easily perform the input operation of the provision agreement information and the announcement agreement information.

This aspect may be constructed such that the patient terminal can display second mark information indicating to call up an agreement input screen of at least one of the announcement agreement information and the provision agreement information on the reference screen in the predetermined format, can call up the agreement input screen by specifying the displayed second mark information, and is capable of inputting at least one of the announcement agreement information and the provision agreement information on the called agreement input screen.

By constituting in this manner, it is possible to perform the input operation of the provision agreement information and the announcement agreement information quickly and easily by specifying the second mark information displayed on the display screen, during the confirmation of the reference screen on which one portion of the electronic charts and the shared chart is displayed or after the conformation without any delay.

In another aspect of the first medical information system of the present invention, at least one of the plurality of medical terminals can transmit chart request information indicating a request for the use of the shared chart with a distinction between an acute disease and a chronic disease related to the one patient, to the shared server apparatus through the communication network, the shared server apparatus transmits the shared chart in a preset form for the acute disease, which preferentially indicates medication records and a previous history of the one patient, out of the patient data included in the shared chart maintained on the shared server apparatus, to the medical terminal which transmits the chart request information, in case that the shared chart about the acute disease is requested, and the shared server apparatus transmits the shared chart in a preset form for the chronic disease, which preferentially indicates a disease name and medication records of the one patient, out of the patient data included in the shared chart maintained on the shared server apparatus, to the medical terminal which transmits the chart request information, in case that the shared chart about the chronic disease is requested.

According to this aspect, when a patient who has the acute disease is examined and treated at any one of the medical-related facilities, any one of the medical terminals transmits the chart request information indicating a request for the use of the shared chart with the distinction of the acute disease, to the shared server apparatus. Receiving this information, the shared server apparatus sends back the shared chart in the preset form for the acute disease, which preferentially indicates medication records and a previous history, out of the patient data. At the medical-related facility at which the medical care and the treatment thereof will be performed, it is possible to refer to the shared chart which includes information about the medication records and the previous history (allergy or the like) for implementing appropriate prescriptions and tests, which are more important about the acute disease from the medical viewpoint. Therefore, it is possible to provide high quality medication for the patient who has the acute disease.

On the other hand, when a patient who has the chronic disease is examined and treated at any one of the medical-related facilities, any one of the medical terminals transmits the chart request information indicating a request for the use of the shared chart with the distinction of the chronic disease, to the shared server apparatus. Receiving this information, the shared server apparatus sends back the shared chart in the preset form for the chronic disease, which preferentially indicates a disease name and medication records, out of the patient data. At the medical-related facility at which the medical care and the treatment thereof will be performed, it is possible to refer to the shared chart which includes information about the disease name, e.g. diabetes, and the medication records, which are more important about the chronic disease from the medical viewpoint. Therefore, it is possible to provide high quality medication for the patient who has the chronic disease.

In another aspect of the first medical information system of the present invention, at least one of the plurality of medical terminals can display a screen for providing medical care, which is intended to perform email medical care through the communication network with the patient terminal, with the screen for providing medical care being switched from display of the electronic chart or the shared chart, the patient terminal can display a screen for receiving medical care, which is intended to receive the email medical care through the communication network with at least one of the medical terminals, with the screen for receiving medical care being switched from display of the patient participatory chart, and the medical server apparatus and the patient server apparatus reflect patient data newly inputted through the screen for providing medical care and the screen for receiving medical care to the electronic chart and the patient participatory chart, respectively.

According to this aspect, on the medical terminal side, the screen for providing medical care is displayed, with the screen being switched from the display of the electronic chart or the shared chart. On the patient terminal side, the screen for receiving medical care is displayed, with the screen being switched from the display of the patient participatory chart. This allows the email medical care (including the first consultation and a repeat consultation) through the communication network. Then, the patient data newly inputted through the screen for providing medical care and the screen for receiving medical care during the email medical care in this manner is reflected in the electronic charts and the patient participatory chart. Consequently, the electronic charts, the shared chart, and further the patient participatory chart can be updated without any delay.

In another aspect of the first medical information system of the present invention, the patient terminal is capable of specifying, as a search object, a term described on the patient participatory chart by an input operation of a predetermined type, on a display screen of the patient participatory chart provided from the patient server apparatus, and the patient server apparatus further calls up a site, which is operated by the patient server apparatus or another server apparatus, for searching for the term through the communication network in case that the term is specified as the search object, and provides the site for the patient terminal.

According to this aspect, on the patient terminal side, when the patient's unknown or unused term is included in the patient participatory chart, the term is specified as the search object by input operation of a predetermined type on the display screen of the patient participatory chart. Then, the patient server apparatus calls up a site, which is operated by the patient server apparatus or another server apparatus, through the communication network in order to search for the specified term. Then, the patient server apparatus provides it for the patient terminal side. Therefore, the patient can simply and quickly search for this term displayed on the display screen of the patient participatory chart by using the exclusive site for searching, and can understand the meaning easily.

The above object of the present invention can be achieved by a second medical information system provided with: a medical server apparatus for providing an electronic chart, which includes patient data related to medical care of one patient made or obtained through each of a plurality of medical terminals placed at a plurality of medical-related facilities in one area, for the plurality of the medical terminals for each of the medical-related facilities; and a patient server apparatus capable of providing a patient participatory chart, which at least partially includes the electronic chart provided from the medical server apparatus and which includes patient data related to predetermined items made or obtained through a patient terminal operated by the one patient, for the patient terminal, wherein the medical server apparatus, the patient server apparatus, the plurality of medical terminals, and the patient terminal are included in a communication network, at least one of the plurality of medical terminals and the patient terminal is capable of inputting announcement agreement information indicating agreement of the one patient about medical announcement, and is capable of transmitting the inputted announcement agreement information through the communication network, the patient server apparatus (i) provides the patient participatory chart for the patient terminal in case that the one patient agrees about the medical announcement and (ii) does not provide the patient participatory chart for the patient terminal in case that the one patient disagrees about the medical announcement, on the basis of the announcement agreement information transmitted through the communication network, the patient terminal is capable of specifying, as a search object, a term described on the patient participatory chart by an input operation of a predetermined type, on a display screen of the patient participatory chart provided from the patient server apparatus, and the patient server apparatus further calls up a site, which is operated by the patient server apparatus or another server apparatus, for searching for the term through the communication network in case that the term is specified as the search object, and provides the site for the patient terminal.

According to the second medical information system of the present invention, the medical server apparatus provides the electronic chart including patient data made or obtained through each of the plurality of medical terminals, for the plurality of the medical terminals, as is the case of the above-described first medical information system. The patient server apparatus can provide the patient participatory chart for the patient terminal, as is the case of the above-described first medical information system. As described above, the presence of the shared chart, in addition to the presence of the electronic magnetic charts, gives various benefits to both the patient and the medical-related facilities. Moreover, the use of the announcement agreement information further gives various benefits.

In particular, on the patient terminal side, when the patient's unknown or unused term is included in the patient participatory chart, the term is specified as the search object by the input operation of a predetermined type on the display screen of the patient participatory chart. For example, the term is specified by cursor operation with a mouse or a keyboard. Then, the patient server apparatus calls up a site, which is operated by the patient server apparatus or another server apparatus in order to search for the specified term. Then, the patient server apparatus provides it for the patient terminal side. For example, a browser screen of the called site is displayed by screen switching and window displaying. Therefore, the patient can simply and quickly search for this term by using the exclusive site for searching, and can understand the meaning easily. In particular, according to the structure of the second medical information system of the present invention, even if the patient agrees about the announcement, the patient is an amateur about medical care in many cases, so that the making of and reference to the patient participatory chart come with the patient's worries, non-understanding, misunderstanding, or the like. Therefore, it is extremely useful to have the patient understand the meaning of the term described on the patient participatory chart, in order to give a significance to the making of and reference to the patient participatory chart or in order to operate them smoothly.

As described above, according to the second medical information system, it enables the patient to selectively make and refer to the patient participatory chart, and it decreases the patient's worries and misunderstanding coming with the making of and reference to the patient participatory chart. Therefore, it is possible to smoothly make and refer to the patient participatory chart.

In one aspect of the second medical information system of the present invention, or in the aspect related to the site for researching of the first medical information system of the present invention, the patient server apparatus provides the site for the patient terminal while showing information indicating the meaning of the specified term.

By constituting in this manner, when the term is specified to search for on the patient terminal side, the patient server apparatus calls up the site, which is operated by the patient server apparatus or another server apparatus, for searching for this specified term. Moreover, the patient server apparatus provides this site for the patient terminal while showing information indicating the meaning of the specified term. For example, a browser screen of the called site is displayed by screen switching and window displaying, including a screen portion which text-displays the meaning of the term specified to search for. Therefore, the patient can search for this term extremely quickly by a simple operation and can understand the meaning quickly.

In another aspect of the first or second medical information system of the present invention, the patient terminal is capable of inputting or changing and transmitting the announcement agreement information as well as patient identification information indicating identification of the one patient and a password corresponding to the patient identification information, and the patient server apparatus takes the inputted or changed announcement agreement information to be valid in case that the one patient can be identified by verifying the patient identification information and password transmitted through the communication network.

According to this aspect, the announcement agreement information is transmitted from the patient terminal to the patient server apparatus, as well as the patient identification information and the password (e.g. an encryption key). Then, when the patient can be identified by verifying the patient identification information and password, the patient server apparatus takes the announcement agreement information to be valid, and performs the subsequent making and provision of the patient participatory chart. Therefore, it is possible to prevent effectively that a third person, e.g. a person who pretends to be the patient, improperly urges the making and provision of the patient participatory chart and improperly refers to this chart.

In another aspect of the first or second medical information system of the present invention, the patient terminal cannot change a patient data portion related to items which are different from the predetermined items that can be inputted by the one patient and which are inputted through the medical server apparatus, and can add correction demand information indicating a demand of correction with respect to the patient data portion if desired.

According to this aspect, even when mistakes, errors, or the like are found in the patient data portion related to the items which are different from the predetermined items that can be inputted out of the patient participatory chart, this patient data portion cannot be changed on the patient terminal side. Therefore, it is possible to guarantee a copyright owned on the medical-related facilities which make the patient data portion. At the same time, when mistakes, errors, or the like are found, the correction demand information indicating a demand of correction can be added from the patient terminal side to the patient data portion. Therefore, it is possible to guarantee the right to demand the correction of information about the patient's own charts owned on the patient side.

In another aspect of the first or second medical information system of the present invention, particular matter information which is not to be written in the patient participatory chart can be inputted from at least one of the plurality of medical terminals, and the patient server apparatus provides the patient participatory chart in a form of removing the particular matter information for the patient terminal in case that the one patient agrees about the medical announcement on the basis of the provision agreement information.

According to this aspect, the particular matter information which can be inputted from the medical terminals and which is not to be written in the patient participatory chart is not included in the patient participatory chart provided from the patient server apparatus, even in case that the one patient agrees about the medical announcement on the basis of the provision agreement information. Namely, it is not necessary to let the patient know about this particular matter information.

In another aspect of the first or second medical information system of the present invention, the patient server apparatus judges whether or not the patient data constituting the patient participatory chart is abnormal in accordance with a predetermined standard, extracts the abnormal patient data and a patient participatory chart portion including the patient data related to the abnormal patient data when it is judged as a judgment result that the patient data is abnormal, and provides the extracted patient participatory chart portion for the patient terminal, and the patient terminal can output the provided patient participatory chart portion in a predetermined format.

According to this aspect, not only the patient participatory chart is displayed without exception, but also the abnormal patient data and the patient participatory chart portion including the patient data related to the abnormal patient data are displayed and outputted, or printed and outputted, on the patient terminal side. Thus, it is possible to refer to the patient participatory chart with a focus on a part which has a high possibility to have problems on the patient's own health. Therefore, the present invention is extremely useful in practice in saving time for and avoiding trouble for the reference to the charts on the patient side which is unused to refer to the charts. Moreover, the present invention is extremely useful, as it can decrease the possibility that when there is an important problem, the important problem is overlooked on the patient side which is unused to refer to the charts.

The above object of the present invention can be achieved by a first computer program product in a computer-readable medium for tangibly embodying a program of instructions executable by a computer to make the computer function as the first or second medical information system (including their various aspects).

The above object of the present invention can be achieved by a second computer program product in a computer-readable medium for tangibly embodying a program of instructions executable by a computer to make the computer function as the medical server apparatus, the patient server apparatus, or the shared server apparatus provided in the first or second medical information system (including their various aspects).

According to the first or second computer program product of the present invention, the above described first or second medical information system of the present invention, or the medical server apparatus, the patient server apparatus, or the shared server apparatus can be embodied relatively readily, by loading the computer program product from a recording medium for storing the computer program product, such as a ROM (Read Only Memory), a CD-ROM (Compact Disc—Read Only Memory), a DVD-ROM (DVD Read Only Memory), a hard disk or the like, into the computer, or by downloading the computer program product, which may be a carrier wave, into the computer via a communication device. More specifically, the computer program product may include computer readable codes to cause the computer (or may comprise computer readable instructions for causing the computer) to function as the above-described first or second medical information system of the present invention, or as the medical server apparatus, the patient server apparatus, or the shared server apparatus.

The nature, utility, and further features of this invention will be more clearly apparent from the following detailed description with reference to preferred embodiments of the invention when read in conjunction with the accompanying drawings briefly described below.

DETAILED DESCRIPTION OF THE PREFERRED EMBODIMENTS

The embodiments of the present invention will be explained with reference to the drawings hereinafter.

<1; First Embodiment>

A first embodiment related to the medical information system of the present invention will be explained with reference to FIG. 1 to FIG. 6.

<1-1; Structure of Medical Information System>

Figure 1:
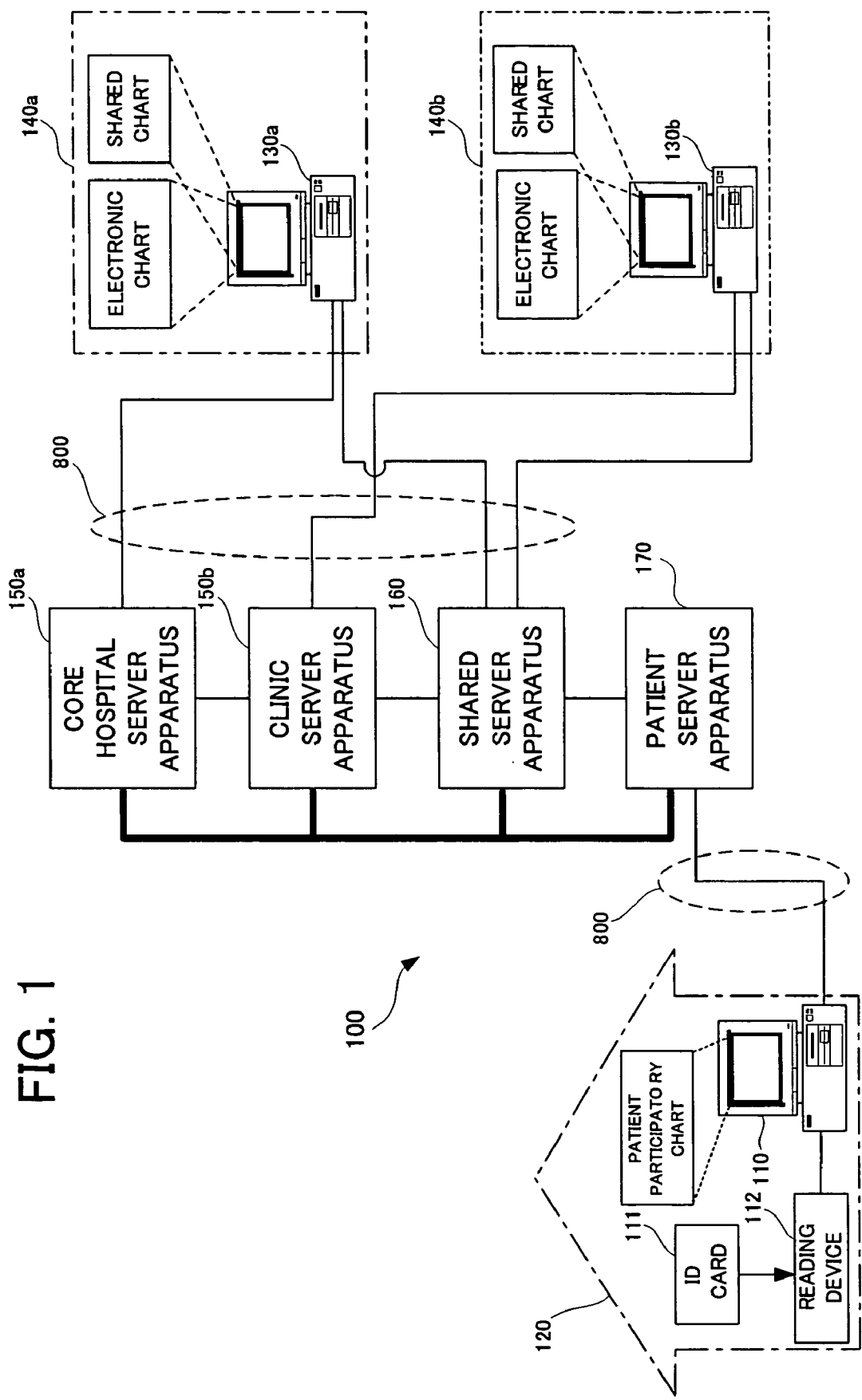
FIG. 1 is a block diagram showing the structure of a medical information system in a first embodiment.

Firstly, the basic structure of the medical information system in the first embodiment will be explained with reference to FIG. 1. FIG. 1 shows the structure of a medical information system in the first embodiment.

In FIG. 1, a medical information system 100 is provided with: a plurality of medical terminals 130 (130a and 130b) respectively placed at a plurality of medical-related facilities 140 (140a and 140b, respectively), such as a core hospital, general hospitals, and clinics, in one area; a plurality of medical server apparatuses 150 (150a and 150b) placed for the plurality of medical-related facilities 140; a patient terminal 110 placed at a patient A's home 120, for example; a patient server apparatus 170 placed for the patient terminal 110; and a shared server apparatus 160.

FIG. 1 shows that one medical terminal 130a is placed at the core hospital 140a and that another medical terminal 130b is placed at the clinic 140b. The medical terminals 130a and 130b may be personal computers, workstations, or the like. Incidentally, in the explanation below, the medical terminal 130a placed at the core hospital 140a is regarded as a first medical terminal 130a, and the medical terminal 130b placed at the clinic 140b is regarded as a second medical terminal 130b.

In FIG. 1, the core hospital server apparatus 150a is placed for the core hospital 140a as the medical server apparatus, and the clinic server apparatus 150b is placed for the clinic 140b as the medical server apparatus. FIG. 1 shows that the patient terminal 110 is placed at the patient A's home 120. The patient terminal 110, however, may be carried by the patient A. The patient terminal 110 may be a personal computer, a mobile device, a mobile phone, or the like.

According to the first embodiment, the first and second medical terminals 130a and 130b and the patient terminal 110 are included in a communication network, such as the Internet and an intranet, together with the core hospital server apparatus 150a, the clinic server apparatus 150b, the patient server apparatus 170, and the shared server apparatus 160. In FIG. 1, the first and second medical terminals 130a and 130b and the patient terminal 110 are connected to the communication network through a connection device 800, such as the Internet, an intranet, a leased line, a phone line, a wire line, and a wireless line.

In this embodiment, the clinic server apparatus 150b, the patient server apparatus 170, and the shared server apparatus 160 may be collectively placed at a computer facility, a server facility, or the like, which is placed in the core hospital 140a, for example, together with the core hospital server apparatus 150a. Alternatively, they may be collectively placed at a server facility or the like, which is placed separately from the hospital. Moreover, the core hospital server apparatus 150a may be placed in the core hospital 140a, and the clinic server apparatus 150b may be placed at a dedicated server facility, which is placed separately from the hospital. Furthermore, only the shared server apparatus 160 may be placed at a public or semi governmental dedicated server facility, for example. As long as the apparatuses are connectable through various communication networks, a variety of placement forms of the server apparatuses and inclusion forms thereof in the communication networks are conceivable.

In this embodiment, the core hospital server apparatus 150a and the clinic server apparatus 150b individually provide electronic charts (i.e., electronic clinical charts) for each medical-related facility. In FIG. 1, the core hospital server apparatus 150a provides the first medical terminal 130a placed at the core hospital 140a with an electronic chart through the connection device 800. The first medical terminal 130a operates its browser, for example, allowing the provided electronic chart to be referred. The clinic server apparatus 150b provides the second medical terminal 130b with an electronic chart, as with the core hospital server apparatus 150a, and the electronic chart can be referred on the second medical terminal 130b, as with the first medical terminal 130a.

In this embodiment, patient data can be made and referred on the electronic charts by the first medical terminal 130a and the second medical terminal 130b. More specifically, the first medical terminal 130a and the second medical terminal 130b allow the reference to and making of the following information as the patient data: information about the patient A's medical care, such as examination results and reports about the patient A's medical care; information about a letter of introduction indicating to introduce the patient A to another medical-related facility; information about the reservation of the patient A's medical examination; or the like. Particularly by selecting a browser, the patient data can be referred in various formats, such as time-series display, graphical representation, laboratory test result display, and reference image display.

The patient data can be also obtained from each other by the first medical terminal 130a and the second medical terminal 130b individually using the electronic charts with their browsers as described above. Alternatively, the patient data can be obtained from another medical terminal which is not illustrated in FIG. 1.

The first medical terminal 130a allows the reference to the patient data made or obtained through the first medical terminal 130a, on the electronic chart. Moreover, the second medical terminal 130b allows the reference to the electronic chart, as with the first medical terminal 130a.

Thus, the core hospital 140a can make the core hospital server apparatus 150a manage and maintain the electronic chart, which is used at its own facility, on the first medical terminal 130a, through the connection device 800. The clinic 140b also can manage and maintain the electronic chart, as with the core hospital 140a.

In this embodiment, the patient terminal 110 is preferably used by the patient A, who has an identification card 111 previously distributed, such as an Integrated Circuit (IC) card. The identification card 111 includes a memory which is not illustrated in FIG. 1, and the memory preferably holds or stores therein patient identification information, such as ID, and a password, such as an encryption key. A reading device 112 for reading information stored in the memory of the identification card 111 is connected to the patient terminal 110.

The patient server apparatus 170 is constructed such that it can provide a patient participatory chart for the patient terminal 110 through the connection device 800. The patient terminal 110 operates its browser, for example, allowing the provided patient participatory chart to be referred. In this embodiment, the patient data on the patient participatory chart can be referred on the patient server apparatus 110.

In this embodiment, the electronic charts are provided for the patient server apparatus 170 from the core hospital server apparatus 150a and the clinic server apparatus 150b, which are included in the same communication network. The patient server apparatus 170 makes the patient participatory chart at least partially including the electronic charts provided in this manner, and provides the patient terminal 110 with it.

The patient terminal 110 allows the making of the patient data related to predetermined items on the patient participatory chart.

The patient terminal 110 allows the reference to the patient data related to predetermined items made on the patient terminal 110 and the reference to the patient data made or obtained on the first medical terminal 130a and the second medical terminal 130b, on the patient participatory chart.

Incidentally, in this embodiment, the reading device 112 can be placed at the first medical terminal 130a and the second medical terminal 130b. By constituting in this manner, the patient A, who has the identification card 111, can refer to the patient data on the patient participatory chart through the first medical terminal 130a and the second medical terminal 130b even at the core hospital 140a and at the clinic 140b, as with the patient terminal 110.

The shared server apparatus 160 makes a shared chart integrally for each patient and provides the made shared chart for any one of the first medical terminal 130a and the second medical terminal 130b in FIG. 1 through the connection device 800.

In this embodiment, the electronic charts are provided for the shared server apparatus 160 from the core hospital server apparatus 150a and the clinic server apparatus 150b, which are included in the same communication network. In the meanwhile, the patient participatory chart is provided for the shared server apparatus 160 from the patient server apparatus 170 included in the same communication network. The shared server apparatus 160 makes the shared chart at least partially including both the electronic charts and the patient participatory chart provided in this manner.

Thus, at the core hospital 140a, the first medical terminal 130a allows the reference to the patient data made by or obtained from the second medical terminal 130b, in addition to the patient data by the first medical terminal 130a, on the shared chart. At the clinic 140b, the second medical terminal 130b allows the reference to the patient data on the shared chart, as with the first medical terminal 130a. Therefore, at the core hospital 140a and the clinic 140b, it is possible to improve the quality of medical care by individually using the shard chart in the above-explained manner. Moreover, the patient participatory chart, which is made with the patient A's participation as described above, is also included in the shared chart, so that the shared chart helps improve more the quality of medical care at the core hospital 140a and the clinic 140b.

As described above, the presence of the shared chart which can also monogenetically include the patient participatory chart and its contents, in addition to the presence of the electronic magnetic charts, gives various benefits to both the patient A and the medical-related facilities.

However, only for the reason of convenience, if the patient A is allowed to simply make and refer to the patient participatory chart, the patient A might know his illness and health conditions while making and referring to the patient participatory chart. On the other hand, because it is considered that the patient A has the right to browse or use the electronic chart made at each medical-related facility or the right to license the browsing and use, there is a requirement for a technique in which these inherent rights to the patient A are supposed to be respected. However, if the shared chart is made simply by a third-party institution except the patient A, this may cause the lack of patient privacy protection.

Therefore, in FIG. 1, at least one of the first medical terminal 130a, the second medical terminal 130b, and the patient terminal 110 is constructed such that it can input and transmit announcement agreement information and provision agreement information. Incidentally, the input and transmission of the announcement agreement information and the provisions agreement information will be explained in detail later.

On the patient server apparatus 170 side, the patient participatory chart is made on the basis of the announcement agreement information, which is inputted on the patient terminal 110, the first medical terminal 130a, and the second medical terminal 130b and which is transmitted to the communication network through the connection device 800, under the condition that the patient A agrees about the announcement. Then, the patient participatory chart is provided for the patient terminal 110, and the chart is allowed to be referred and recorded by the patient A on the patient terminal 110 side. Incidentally, control performed by the patient server apparatus 170 of this type will be explained in detail later.

In the meanwhile, on the shared server apparatus 160 side, the content written by the patient A himself of the patient participatory chart, which is made with the patient A's participation, is incorporated in the monogenetic shared chart under the condition that the patient A agrees about the provision on the basis of the provision agreement information, which is inputted on the patient terminal 110, the first medical terminal 130a or the second medical terminal 130b as described above and which is transmitted to the communication network through the connection device 800. Incidentally, control performed by the shared server apparatus 160 of this type will be explained in detail later.

<1-2; Operation of Medical Information System>

Next, the operation of the medical information system will be explained with reference to FIG. 2 to FIG. 6.

Figure 2:
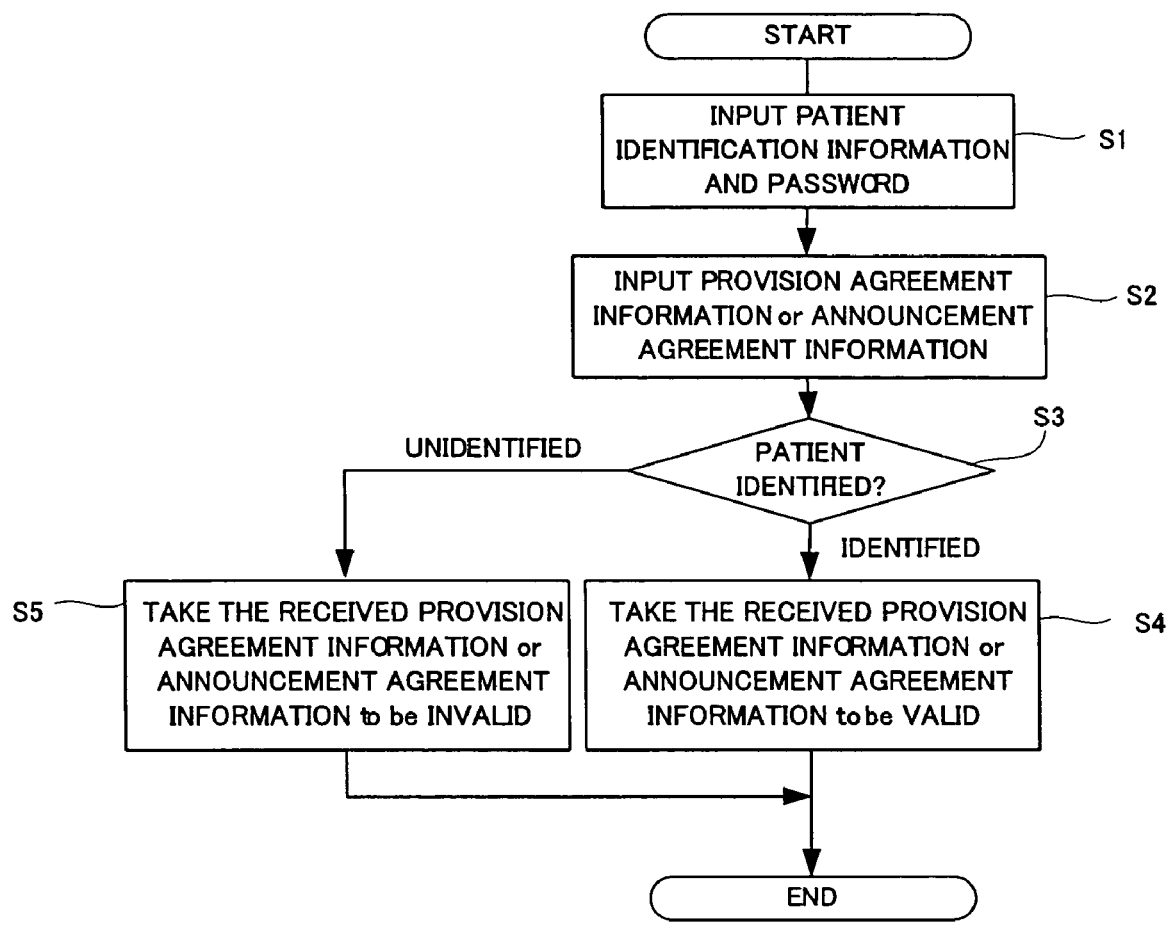
FIG. 2 is a flowchart showing one operation of the medical information system in the first embodiment.

Firstly, operations related to the input of the provision agreement information and the announcement agreement information performed through the patient terminal 110 will be explained with reference to FIG. 2. FIG. 2 shows the operations related to the input of the provision agreement information and the announcement agreement information.

In FIG. 2, firstly, through the reading device 112, the patient identification information and the password, which are read from the identification card 111 by the reading device 112, are inputted to the patient terminal 110 (step S1).

Next, the patient terminal 110 displays an input screen which leads (i.e., inspires or urges) the patient A, who operates the patient terminal 110, to input the provision agreement information and the announcement agreement information. The provision agreement information or the announcement agreement information is inputted through an input device, such as a mouse (step S2). For example, the provision agreement information or the announcement agreement information is inputted in the following way.

Figure 3:
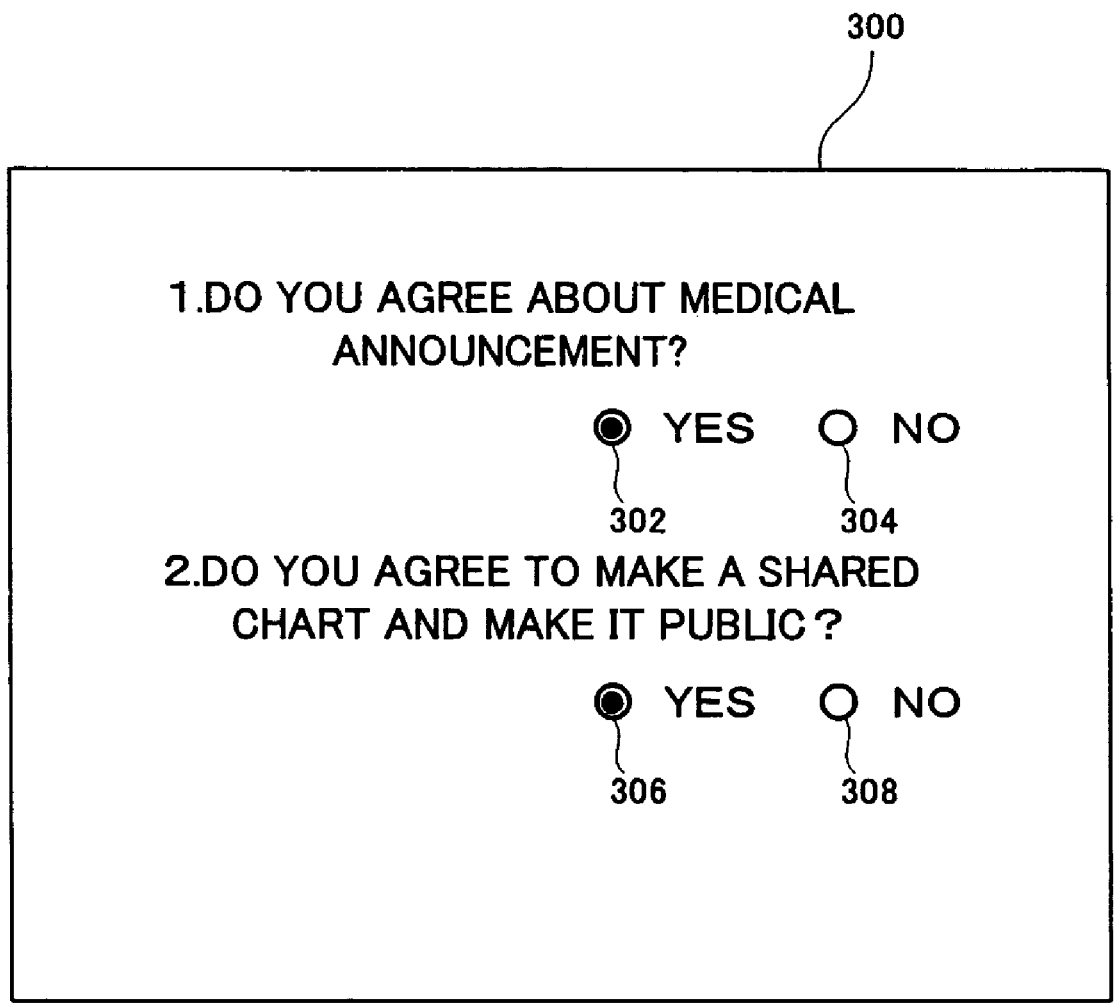
FIG. 3 is a schematic diagram showing one example of an input screen to input provision agreement information and announcement agreement information.

FIG. 3 shows one example of the input screen to input the provision agreement information or the announcement agreement information. In FIG. 3, a question "Do you agree about medical announcement?" is displayed on an input screen 300 in order to lead the input of the announcement agreement information, and a question "Do you agree to make a shared chart and make it public?" is displayed on the input screen 300 in order to lead the input of the provision agreement information. In order to input information indicating his agreement, with respect to the question "Do you agree about medical announcement?", the patient A clicks on an input portion 302 on the left of "YES" displayed on the input screen 300, by using a mouse, for example. Moreover, the patient A clicks on an input portion 306 on the left of "YES" displayed on the input screen 300, by using a mouse, for example, with respect to the question "Do you agree to make a shared chart and make it public?", inputting the provision agreement information.

Incidentally, in this embodiment, screens may be individually displayed for the input of the announcement agreement information and the provision agreement information.

Again in FIG. 2, the patient terminal 110 transmits the patient identification information and password inputted to the patient terminal 110 in the above manner, as well as the provision agreement information and the announcement agreement information.

Then, the shared server apparatus 160 receives the patient identification information, the password, and the provision agreement information through the connection device 800, and identifies the patient A in response to the reception (step S3). Also, the patient server apparatus 170 receives the patient identification information, the password, and the announcement agreement information through the connection device 800, and identifies the patient A in response to the reception (step S3). More specifically, the shared server apparatus 160 or the patient server apparatus 170 identifies the patient A by verifying the received patient identification information and password.

When it can identify the patient A by verifying the patient identification information and the password (the step S3: identified), the shared server apparatus 160 takes the received provision agreement information to be valid (step S4). When it cannot identify the patient A by verifying the patient identification information and the password (the step S3: unidentified), the shared server apparatus 160 takes the received provision agreement information to be invalid (step S5). Then, the shared server apparatus 160 maintains the valid provision agreement information after relating it to the identified patient identification information and password.

At the same time of this, or shortly before or after this, when it can identify the patient A by verifying the patient identification information and the password (the step S3: identified), the patient server apparatus 170 takes the received announcement agreement information to be valid (the step S4). When it cannot identify the patient A by verifying the patient identification information and the password (the step S3: unidentified), the patient server apparatus 170 takes the received announcement agreement information to be invalid (the step S5). Then, the patient server apparatus 170 maintains the valid announcement agreement information in the same manner of maintaining the valid provision agreement information.

Then, a series of operations related to the input of the provision agreement information and the announcement agreement information is ended in the medical information system.

Incidentally, with respect to the operation in the step S2, when the patient A clicks on the input portion 302 on the left of "NO" displayed on the input screen 300 and inputs information indicating his disagreement about the medical announcement, with respect to the question "Do you agree about medical announcement?", the patient server apparatus 170 takes the medical announcement agreement information to be invalid if the patient A can be identified by the operation in the step S3. Moreover, in the operation in the step S2, when the patient A inputs information indicating his negative opinion, with respect to the question "Do you agree to make a shared chart and make it public?", the shared server apparatus 160 also takes the provision agreement information to be invalid, as is the case where information indicating his disagreement about the medical announcement is inputted.

Incidentally, in FIG. 3, it is also possible to construct the system such that an input screen to which the provision agreement information and the announcement agreement information can be inputted is displayed on the patient terminal 110 after the identification of the patient A (the step S3) (and only when the patient A can be identified).

Figure 4:
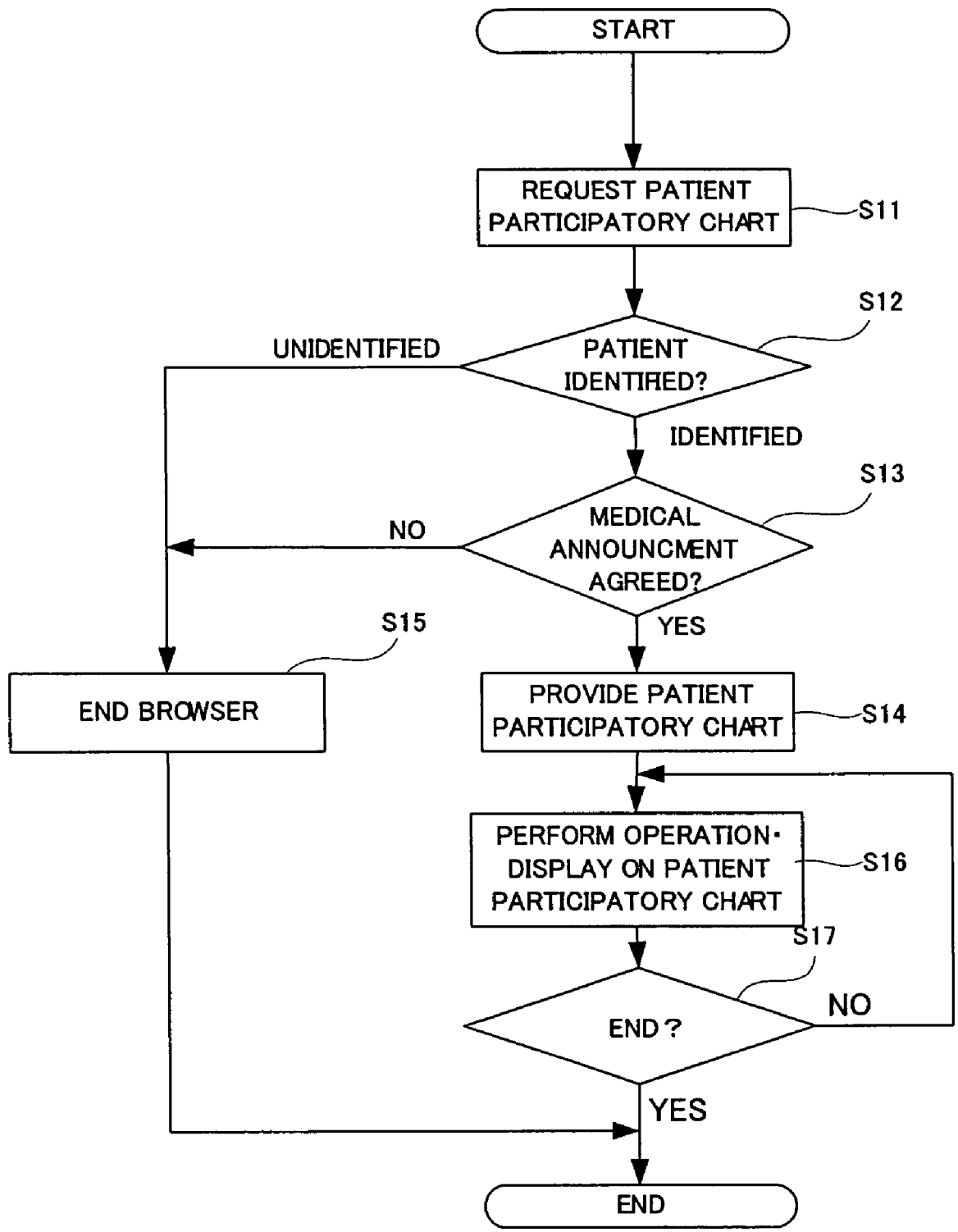
FIG. 4 is a flowchart showing another operation of the medical information system in the first embodiment.

Next, operations related to the provision of the patient participatory chart by the patient server apparatus 170 will be explained with reference to FIG. 4. FIG. 4 shows the operations related to the provision of the patient participatory chart.

Firstly, the reading device 112 inputs the patient identification information and the password, which is the same operation as that in the step S1 in FIG. 2. The patient terminal 110 transmits the inputted patient identification information and password to the patient server apparatus 170 and requires the provision of the patient participatory chart (step S11).

Then, the patient server apparatus 170 identifies the patient A (step S12), which is the same operation as that in the step S3 in FIG. 2. When it can identify the patient A by verifying the patient identification information and the password (the step S12: identified), the patient server apparatus 170 confirms the announcement agreement information maintained in relation to the identified patient identification information and password (step S13).

When the announcement agreement information is valid (the step S13: YES), i.e. when the patient A, who is related to the identified patient identification information and password, agrees about the medical announcement, the patient server apparatus 170 transmits the patient participatory chart, which is related to the identified patient identification information and password, to the patient terminal 110 (step S14).

In contrast to this case, when it cannot identify the patient A (the step S12: unidentified), or when the announcement agreement information is invalid (the step S13: NO), the patient server apparatus 170 denies the provision of the patient participatory chart. In response to this action, the patient terminal 110 ends its browser (step S15). Then, a series of operations related to the provision of the patient participatory chart is ended.

On the other hand, after the patient participatory chart is provided from the patient server apparatus 170, the following operations are performed on the patient participatory chart on the patient terminal 110 (step S16).

The patient terminal 110 allows the making of the patient data related to predetermined items on the patient participatory chart and allows the reference to the made patient data. Alternatively, it allows the reference to the patient data made or obtained on the first medical terminal 130a and the second medical terminal 130b.

Figure 5A:
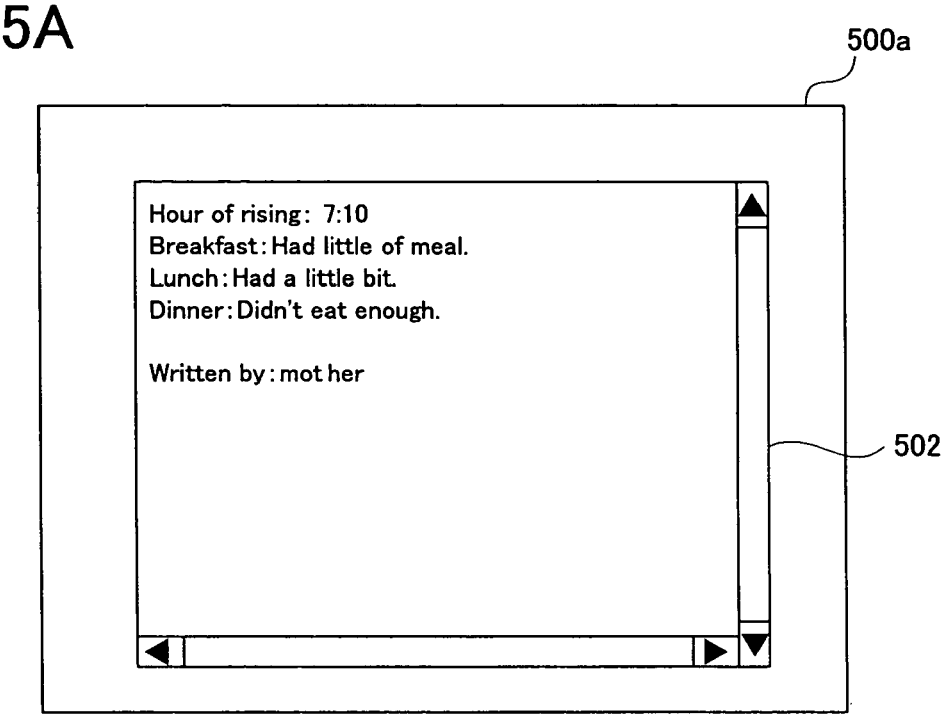
FIG. 5A is a schematic diagram showing one example of an input screen to lead the making of patient data.
Figure 5B:
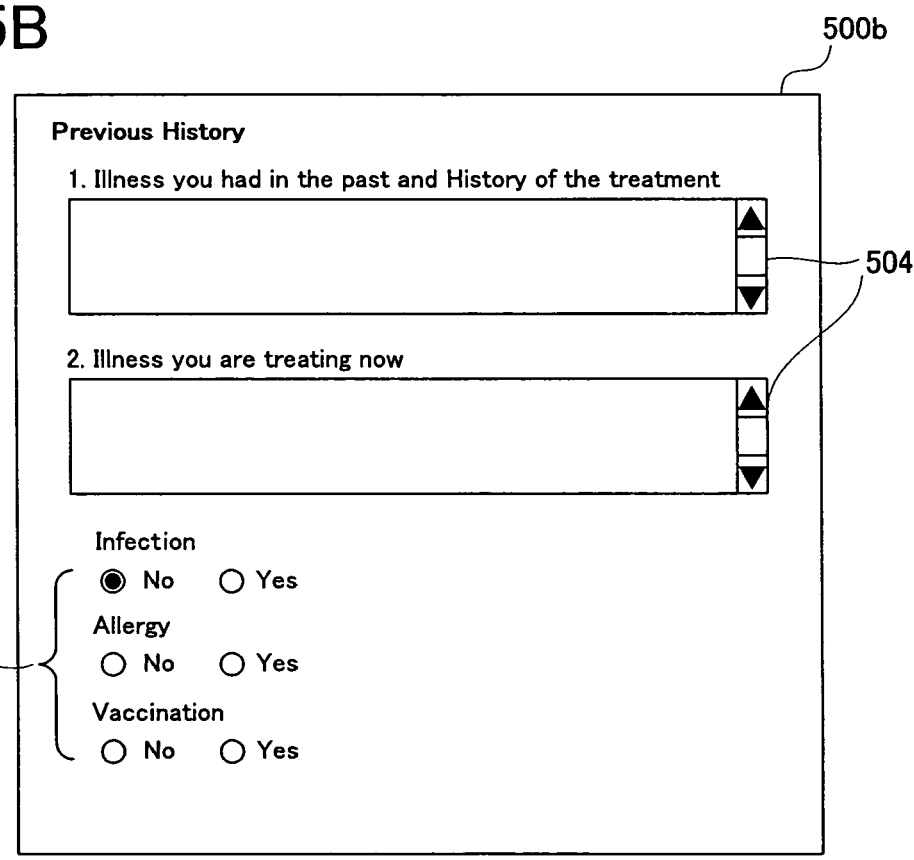
FIG. 5B is a schematic diagram showing another example of the input screen to lead the making of patient data.

FIG. 5A shows one example of the input screen to lead the making of the patient data related to a record of the patient A's questions and concerns as one of the predetermined items. FIG. 5B shows one example of the input screen to lead the making of patient data related to a patient self-supervision record as one of the predetermined items.

An input screen 500a for the record of the patient A's questions and concerns is displayed on the patient terminal 110, as shown in FIG. 5A, for example. The patient A's questions and concerns about his medical care are inputted by keyboard operation or the like and recorded on an input portion 502 on the input screen 500a.

An input screen 500b for the patient self-supervision record is displayed on the patient terminal 110, as shown in FIG. 5B, for example. A template on which the patient A records his own health care situation is displayed, as this input screen 500b. A record related to the patient A's past illness and a record related to the patient A's currently treating illness are text-inputted by keyboard operation or the like, on an input portion 504 on the input screen 500b. Alternatively, a record related to the presence or absence of infections, allergy, or vaccination is inputted by the patient A clicking on an input portion 506 with a mouse, for example.

Moreover, questions, worries, and concerns about medical care and treatment from the patient A's viewpoint, and some requests to the doctor side or the like are inputted as the "predetermined items" on the patient participatory chart, with the patient A himself as a data supply source. As the "predetermined items", the following is conceivable: "an evaluation record" for the patient A recording the evaluation of details of medical care; "a request record" for the patient A recording requests about medicines or treatment; or the like.

Then, after various operations are performed on the patient participatory chart on the patient terminal 110, it is judged whether or not to be ended, e.g. whether or not an end command is inputted on the patient terminal 110, on the patient server apparatus 170 side (step S17). As long as it is judged that it is not to be ended at this time (the step S17: NO), the operation and the display as shown in FIG. 5A and FIG. 5B are continued. If it is judged that it is to be ended (the step S17: YES), a series of operations related to the provision of the patient participatory chart is ended.

Thus, in this embodiment, the patient server apparatus 170 provides the patient A's participation on the basis of the announcement agreement information, thereby to control the participation or nonparticipation to the making of the patient participatory chart, or the reference or unreference thereof for each patient. Therefore, on the patient terminal 110 side, the patient participatory chart can be referred under the condition that the patient A himself agrees about the announcement. In this case, there is not much risk of referring to the patient participatory chart by accident and learning own medical conditions or the like although the medical announcement is undesired. Thus, the patient A's rights to browse and refer are respected while the medical announcement problem is solved. Moreover, the patient A's participation to the making of the chart allows the making of the patient participatory chart whose quality is expected to improve more. In particular, the patient A can receive the patient participatory chart on line from anywhere if the patient A is in the environment that the patient A can use the communication network. At the same time, the patient A can also write information or the like on the chart any time. Therefore, it is possible to decrease the possibility that the patient A forgets to record medically important matters.

In this embodiment, when the patient A can be identified by verifying the patient identification information and password transmitted from the patient terminal 110, the patient server apparatus 170 takes the announcement agreement information to be valid, and performs the subsequent making and provision of the patient participatory chart. Therefore, it is possible to prevent effectively that a third person, e.g. a person who pretends to be the patient A, improperly urges the making and provision of the patient participatory chart and improperly refers to this chart.

Moreover, when the patient A can be identified by verifying the patient identification information and password transmitted from the patient terminal 110, the patient server apparatus 170 provides the patient participatory chart for the patient terminal 110. Therefore, it is possible to effectively prevent that a third person, e.g. a person who pretends to be the patient A, refers to the patient participatory chart and further records thereon false information.

Compared with a technique of recording the main patient data on an IC card, not of using the patient server apparatus 170 as described in this embodiment, this embodiment relatively easily enables invalidation operation on invalidating with respect to loss, theft, or the like. Thus, it is extremely suitable to prevent leaks of the patient data.

Moreover, in this embodiment, the identification card 111 can be constructed as an IC card. It is possible to issue not only an IC card for the patient A, but also that for a legal representative and that for family members, such as relatives, or the like. With respect to the patient identification information, it is convenient to add the unified patient identification information to each patient on a plurality of server apparatuses and terminals, which are included in the communication network. If the IC card of this type is used to control the access to the patient server apparatus 170 from the patient terminal 110, the access operation becomes extremely easily for the patient A, who uses the patient terminal 110, which results in effective use of the patient participatory chart.

Incidentally, in FIG. 4, it is also possible to construct such that after the identification of the patient A (the step S12) (and also when the patient A can be identified), an input screen on which the request for the patient participatory chart (the step S11) can be inputted is displayed on the patient terminal 110.

Figure 6:
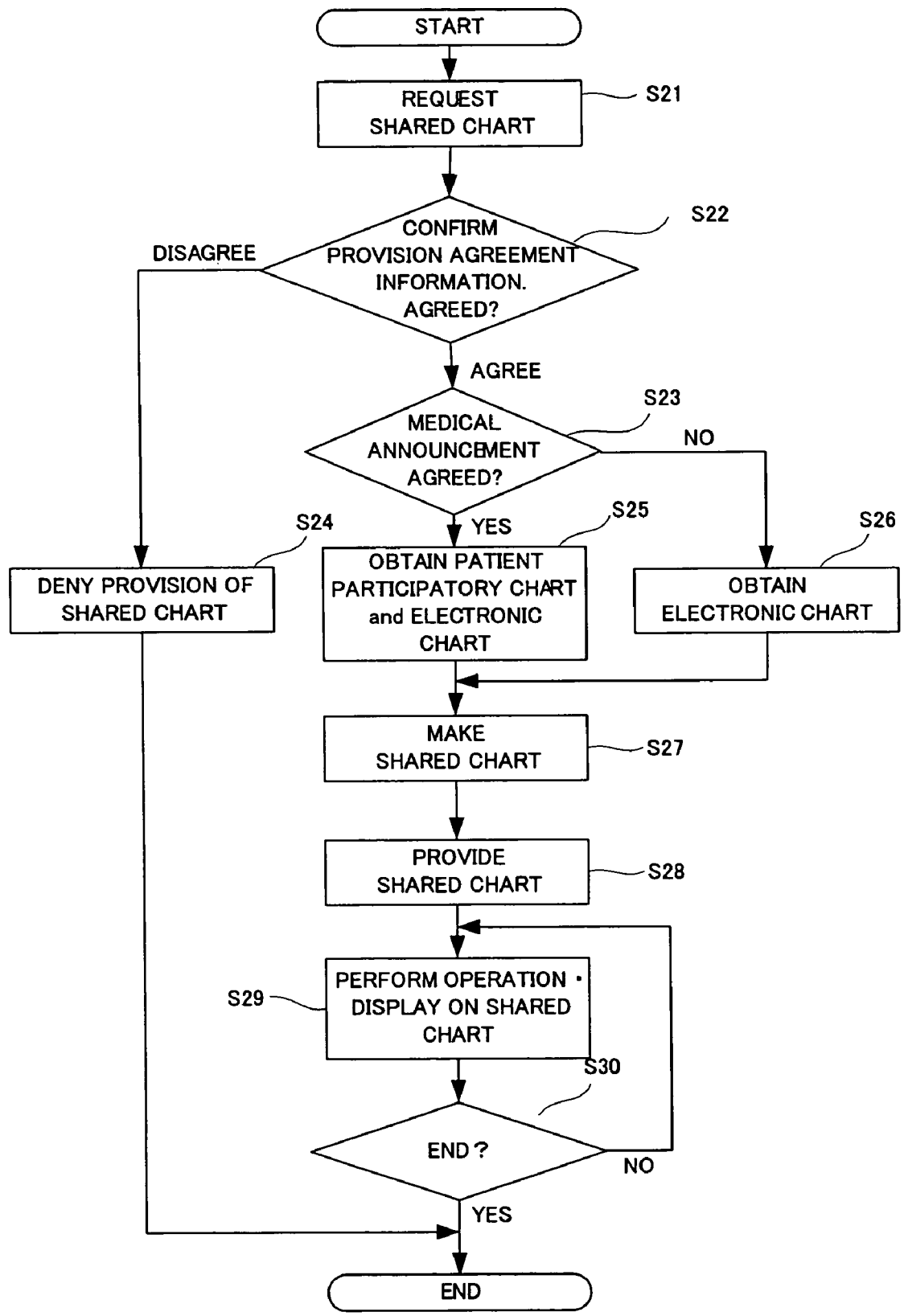
FIG. 6 is a flowchart showing another operation of the medical information system in the first embodiment.

Next, operations related to the provision of the shared chart by the shared server apparatus 160 will be explained with reference to FIG. 6. FIG. 6 shows the operations related to the provision of the shared chart. Incidentally, the case of providing the shared chart for the first medical terminal 130*a* will be explained hereinafter, but the same is true in the case of providing the shared chart for the second medical terminal 130*b* as in the case for the first medical terminal 130*a*.

Firstly, the first medical terminal 130*a* requests the shared server apparatus 160 to provide the shared chart by keyboard operation or the like (step S21).

When receiving a request signal indicating the request for the shared chart, the shared server apparatus 160 confirms the provision agreement information related to the shared chart corresponding to the request signal (step S22).

When the provision agreement information is valid (the step S22: YES), i.e., when the patient A, who is related to the provision agreement information, agrees about the provision of the shared chart, the shared server apparatus 160 further confirms the announcement agreement information related to the shared chart (step S23). More specifically, the shared server apparatus 160 transmits a confirmation signal indicating the confirmation of the announcement agreement information with respect to the patient server apparatus 170. When receiving this confirmation signal, the patient server apparatus 170 confirms the announcement agreement information related to the confirmation signal. Incidentally, not only the patient server apparatus 170 but also the shared server apparatus 160 allow the retention of the announcement agreement information previously maintained for each patient thereon.

In contrast to this case, when the provision agreement information is invalid (the step S22: NO), i.e., when the patient A, who is related to the provision agreement information, disagrees about the provision of the shared chart, the shared server apparatus 160 denies the provision of the shared chart (step S24). In response to this action, the first medical terminal 130*a* ends its browser. Then, a series of operations related to the provision of the shared chart is ended.

When receiving, from the patient server apparatus 170, a signal indicating that the announcement agreement information is valid (the step S23: YES), the shared server apparatus 160 obtains the electronic charts from the core hospital server apparatus 150*a* and the clinic server apparatus 150*b*, as well as the patient participatory chart from the patient server apparatus 170 (step S25). More specifically, the shared server apparatus 160 obtains the electronic charts and the patient participatory chart as follows.

The shared server apparatus 160 requests the core hospital server apparatus 150*a* and the clinic server apparatus 150*b* to provide the electronic charts corresponding to the patient A related to the shared chart.

When receiving a request signal for the electronic charts, the core hospital server apparatus 150*a* and the clinic server apparatus 150*b* provide the electronic charts corresponding to the request signal for shared server apparatus 160 with. When receiving the request signal, the patient server apparatus 170 also provides the patient participatory chart corresponding to the request signal for the shared server apparatus 160.

In contrast to this case, when receiving, from the patient server apparatus 170, a signal indicating that the announcement agreement information is invalid (the step S23: NO), the shared server apparatus 160 obtains the electronic charts from the core hospital server apparatus 150*a* and the clinic server apparatus 150*b* (step S26). The electronic charts are obtained by the shared server apparatus 160 requesting the core hospital server apparatus 150*a* and the clinic server apparatus 150*b* to provide the electronic charts, as in the above-described step S25.

The shared server apparatus 160 makes the shared chart at least partially including the provided electronic charts and patient participatory chart (step S27). Incidentally, after the processing in the step S26, the shared chart at least partially including the obtained electronic charts may be also made on the shared server apparatus 160.

Then, the shared server apparatus 160 transmits the made shared chart to the first medical terminal 130*a* (step S28). After the shared chart is provided from the shared server apparatus 160, the operations on the shared chart is performed on the first medical terminal 130*a* (step S29). More specifically, the operations on the shared chart allows the reference to the patient data made by or obtained from the second medical terminal 130*b*, in addition to the first medical terminal 130*a*. If the patient A agrees about the announcement and thus there is the patient participatory chart including the patient data inputted and made as shown in FIG. 5A and FIG. 5B, the patient participatory chart, which is made with the patient A's participation, is included in the shared chart. Therefore, it is also possible to refer to the patient data made on the patient terminal 110.

After various operations and the display of various aspects are performed on the shared chart on the first medical terminal 130, it is judged whether or not to be ended, e.g. whether or not an end command is inputted on the patient terminal 110, on the patient server apparatus 170 side (step S30). As long as it is judged that it is not to be ended at this time (the step S30: NO), the operation and the display as shown in FIG. 5A and FIG. 5B are continued. If it is judged that it is to be ended (the step S30: YES), a series of operations related to the provision of the shared chart is ended.

As described above, in this embodiment, the shared server apparatus 160 can control the making or unmaking of the shared chart, or the provision or non-provision thereof, for each patient on the basis of the provision agreement information. Therefore, the patient A's electronic chart can be used as one portion of the shared chart, including the content recorded by the patient A himself, not only at the core hospital 150*a* which mainly makes the electronic chart but also at the clinic 140*b* which makes only one portion of the patient A's electronic chart or which does not make it at all.

The provision or non-provision of the electronic charts for the shared server apparatus 160 is controlled individually on the core hospital server apparatus 150*a* and the clinic server apparatus 150*b* on the basis of the provision agreement information individually received through the communication network. Namely, before the shared server apparatus 160 obtains the patient data, the making of the shared chart is stopped. As a result, as long as the patient A agrees about the provision, the shared chart can be made safely and surely.

When it can identify the patient A by verifying the patient identification information and password transmitted from the patient terminal 110, the shared server apparatus 160 takes the provision agreement information to be valid and performs the subsequent making and provision of the patient participatory chart. Therefore, it is possible to prevent effectively that a third person, e.g. a person who pretends to be the patient A, improperly urges the making and provision of the shared chart and improperly refers to this chart.

Incidentally, this embodiment may be constructed such that the patient A can operate the first medical terminal 130*a* or the second medical terminal 130*b* to which the reading device 112 is connected. In this case, the patient identification information and password inputted from the reading device 112 are transmitted by the first medical terminal 130*a* and the second medical terminal 130*b* through the connection device 800. In this case, moreover, the same operations as those of the patient terminal 110 are preferably performed on the first medical terminal 130*a* or the second medical terminal 130*b*.

In this embodiment, when the patient data related to some items is written on the electronic chart, the first medical terminal 130*a* and the second medical terminal 130*b*, or the core hospital server apparatus 150*a* and the clinic server apparatus 150*b* individually add an electronic stamp indicating a recording date and time with respect to the patient data. It is also good even for the patient terminal 110 or the patient server apparatus 170 to add such an electronic stamp in the same manner, when the self-supervision record or the like is added as the patient data by the patient A himself. With respect to the shared server apparatus 160, it is good to maintain the electronic stamps originally added to a plurality of patient data, which is unified in the form of the shard chart. By constituting in this manner, even if there are a plurality of types of charts (i.e. the electronic charts, the patient participatory chart, and the shared chart) for one patient, the patient A, it is possible to avoid the identity, nonidentity, or unclear interrelation of the patient data constituting the charts.

As described above, according to this embodiment, it enables the patient A to selectively make and refer to the patient participatory chart, and it enables the plurality of medical-related facilities to selectively use the shared chart, which is monogenetic and which may include the content of the patient participatory chart. Therefore, it is possible to improve the quality of local medication drastically. At the same time, even from the patient A's view point, it is possible to maximize the charts to help his own medical and health promotion.

Next, the second to eighth embodiments related to the medical information system of the present invention will be explained. The medical information system in each of the second to eighth embodiments has the same structure as that of the medical information system in the first embodiment and performs relatively the same operations. Therefore, in each embodiment, the explanation will be only about the different points from the first embodiment. Incidentally, the structure of the medical information system in each embodiment will be explained with reference to FIG. 1.

<2: Second Embodiment>

Next, the second embodiment related to the medical information system of the present invention will be explained. Its detailed operations related to the provision of the shared chart are different from those in the first embodiment. The operations thereof will be explained with reference to FIG. 6.

In FIG. 1, the electronic charts are provided in advance for the shared server apparatus 160 from the core hospital server apparatus 150*a* and the clinic server apparatus 150*b* in the medical information system in the second embodiment.

On the provision of the shared chart, the processing in the step S25, the step S26, and the step S27 is performed by the following operations. Incidentally, the case of providing the shared chart for the first medical terminal 130*a* will be explained hereinafter, but the same is true in the case of providing the shared chart for the second medical terminal 130*b* as in the case for the first medical terminal 130*a*.

When receiving, from the patient server apparatus 170, a signal indicating that the announcement agreement information is valid (the step S23: YES), the shared server apparatus 160 makes a request only for the provision of the patient participatory chart to the patient server apparatus 170 and obtains the patient participatory chart in the same procedure as that in the first embodiment in the step S25.

In contrast to this case, when receiving, from the patient server apparatus 170, a signal indicating that the announcement agreement information is invalid (the step S23: NO), the processing in the step 26 is not performed but the processing in the step S27 is performed.

In the processing in the step S27, the shared server apparatus 160 makes the shared chart which at least partially includes the previously provided electronic charts and the obtained patient participatory chart. Incidentally, when receiving, from the patient server apparatus 170, a signal indicating that the announcement agreement information is invalid (the step S23: NO), the shared chart at least partially including the previously provided electronic charts may be also made on the shared server apparatus 160.

Thus, in the second embodiment, the making or unmaking of the shared chart is controlled on the shared server apparatus 160 on the basis of the provision agreement information received through the communication network. Namely, after the shared server apparatus 160 obtains the patient data, the making of the shared chart is stopped.

<3: Third Embodiment>

Figure 7:
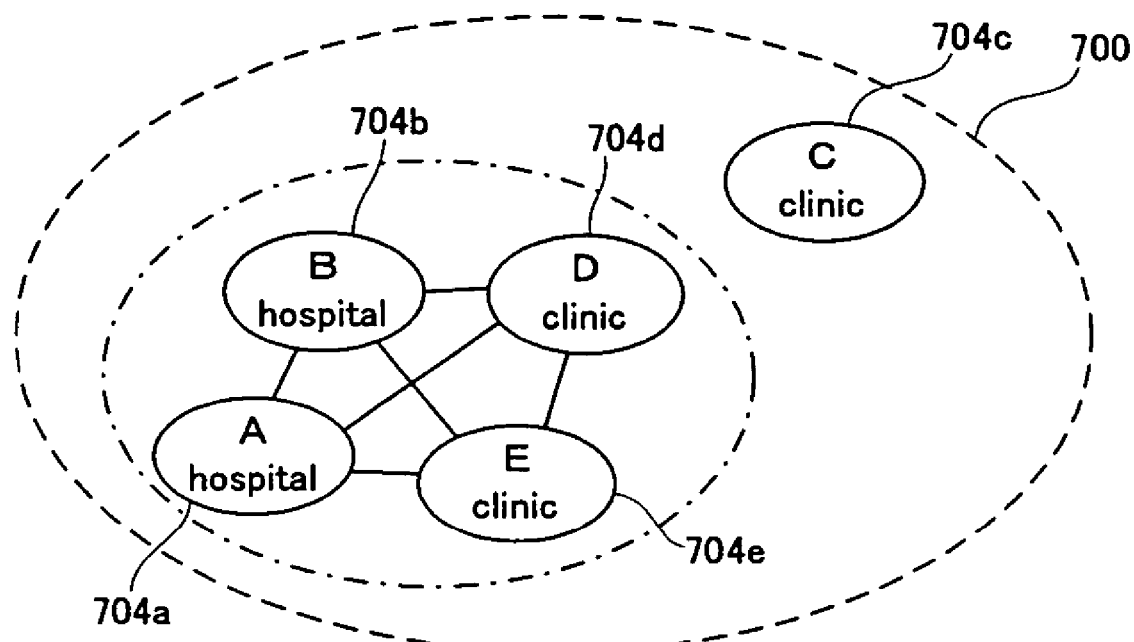
FIG. 7 is a schematic diagram to explain the selection of medical-related facilities by a patient.

Next, the third embodiment related to the medical information system of the present invention will be explained. Its detailed operations related to the input of the provision agreement information and detailed operations related to the provision of the shared chart are different from those in the first embodiment. The operations thereof will be explained with reference to FIG. 2, FIG. 3, FIG. 6, and FIG. 7. FIG. 7 is a schematic diagram to explain the selection of medical-related facilities by a patient.

On the input of the provision agreement information, the processing in the step S2 is performed by the following operations.

On the input of the provision agreement information performed on the input screen 300 explained with reference with FIG. 3, selection information indicating an medical terminal or terminals selected to have the application of the shared chart is inputted by keyboard operation or the like on the patient terminal 110 shown in FIG. 1.

For example, in FIG. 7, a communication network 700 includes: an A hospital 704a as being a core hospital; a B hospital 704b; a C clinic 704c; a D clinic 704d; and an E clinic 704e. Out of them, the A hospital 704a, the B hospital 704b, the D clinic 704d, and the E clinic 704e are selected by one patient. Then, selection information indicating that the medical terminals placed at the A hospital 704a, the B hospital 704b, the D clinic 704d, and the E clinic 704e have the application of the shared chart is inputted. Then, the provision agreement information including the inputted selection information is transmitted from the patient terminal 110.

On the provision of the shared chart, the processing in the step S22, the step S25, the step S26, the step S27, and the step S28 in FIG. 6 is performed by the following operations. Incidentally, medical server apparatuses are individually placed at the medical-related facilities shown in FIG. 7.

In the processing in the step S22, the shared server apparatus 160 confirms the selection information as well as the provision agreement information.

Then, in the processing in the step S25 and the step S26, the shared server apparatus 160 obtains the electronic charts provided from the medical terminals indicated by the selection information, i.e. the electronic charts managed or maintained on the medical server apparatuses corresponding to the A hospital 704a, the B hospital 704b, the D clinic 704d, and the E clinic 704e.

Then, in the processing in the step S27, the shared server apparatus 160 makes the shared chart at least partially including the electronic charts provided from the medical server apparatuses corresponding to the A hospital 704a, the B hospital 704b, the D clinic 704d, and the E clinic 704e.

Then, in the processing in the step S28, the shared server apparatus 160 transmits the made shared chart to any one of the medical terminals placed at the A hospital 704a, the B hospital 704b, the D clinic 704d, and the E clinic 704e.

Thus, in the third embodiment, the electronic chart managed or maintained at the C clinic 704c which is regarded not to have the application of the-shared chart is not included in the shared chart, and the shared chart is not provided for the C clinic 704c.

Therefore, according to the third embodiment, by virtue of the selection information included in the provision agreement information, the patient A can agree about the provision of the shared chart, not for all medical-related facilities without exception, but for each medical-related facility.

Incidentally, this embodiment may be constructed such that even if the electronic chart from the medical-related facility (e.g. the C clinic 704c) which is regarded not to have the application of the shared chart is eliminated from the content of the shared chart, the shared chart is provided to all medical-related facilities equally, including this medical-related facility (e.g. the C clinic 704c). Alternatively, it may be constructed such that while the shared chart is made to equally include even the electronic chart from the medical-related facility which is regarded not to have the application of the shared chart, the made shared chart is not provided for the medical-related facility which is regarded not to have the application of this shared chart.

Suppose that the above-explained third embodiment is applied to the second embodiment. In the processing in the step S27, the shared server apparatus 160 makes the shared chart which at least partially includes the electronic charts provided from the medical server apparatuses corresponding to the A hospital 704a, the B hospital 704b, the D clinic 704d, and the E clinic 704e and which does not include the electronic chart provided from the C clinic 704c. Therefore, even if the third embodiment is applied to the second embodiment, as is in the third embodiment described above, by virtue of the selection information included in the provision agreement information, the patient A can agree about the provision of the shared chart, not for all medical-related facilities without exception, but for each medical-related facility.

<4: Fourth Embodiment>

Figure 8A:
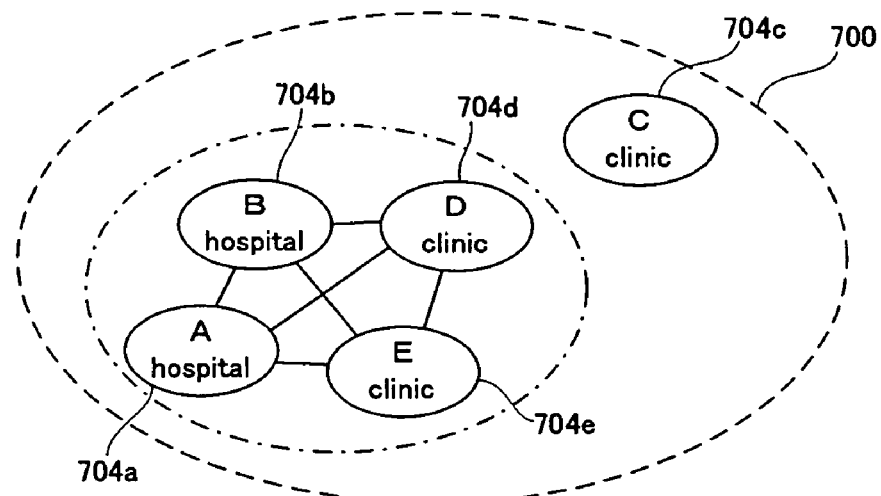
FIG. 8A is a schematic diagram to explain the selection of medical-related facilities, which are patient data sources, by a patient.
Figure 8B:
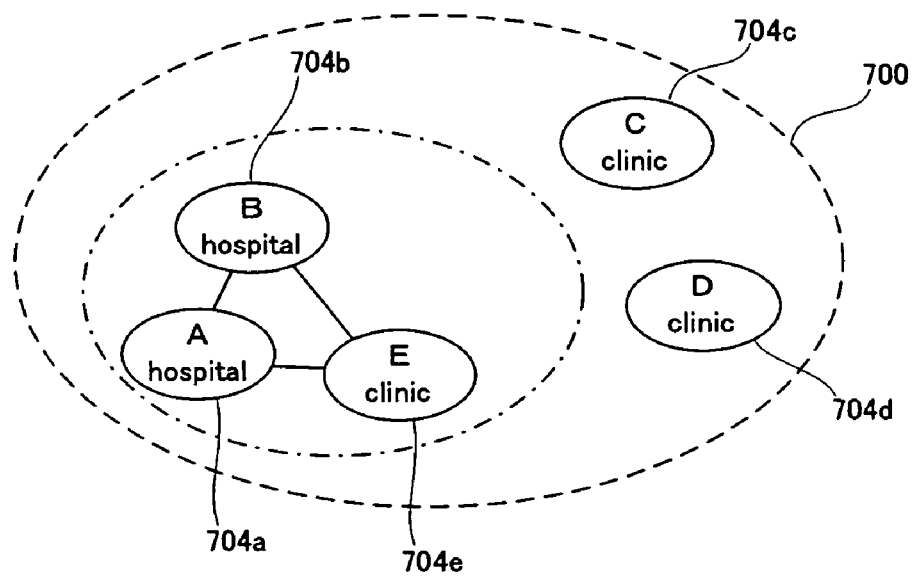
FIG. 8B is a schematic diagram to explain the selection of medical-related facilities, for which a shared chart is provided, by a patient.

Next, the fourth embodiment related to the medical information system of the present invention will be explained. Its detailed operations related to the input of the provision agreement information and detailed operations related to the provision of the shared chart are different from those in the first embodiment. The operations thereof will be explained with reference to FIG. 2, FIG. 3, FIG. 6, FIG. 8A, and FIG. 8B. FIG. 8A explains the selection of medical-related facilities, which are patient data sources, by a patient. FIG. 8B explains the selection of medical-related facilities, for which a shared chart is provided, by a patient.

On the input of the provision agreement information, the processing in the step S2 is performed by the following operations.

On the input of the provision agreement information performed on the input screen 300 explained with reference with FIG. 3, first selection information indicating an medical terminal that is selected to have the application as a "patient data source" of the shared chart and second selection information indicating an medical terminal that is selected to have the application as a "providing destination" of the shared chart is inputted by keyboard operation or the like on the patient terminal 110.

For example, in FIG. 8A, the communication network 700 includes: the A hospital 704a as being a core hospital; the B hospital 704b; the C clinic 704c; the D clinic 704d; and the E clinic 704e. Out of them, the A hospital 704a, the B hospital 704b, the D clinic 704d, and the E clinic 704e are selected by one patient. Then, first selection information indicating that medical terminals placed at the A hospital 704a, the B hospital 704b, the D clinic 704d, and the E clinic 704e are applied as the "patient data sources" is inputted.

Moreover, for example, in FIG. 8B, out of the A hospital 704a as being a core hospital; the B hospital 704b; the C clinic 704c; the D clinic 704d; and the E clinic 704e, the A hospital 704a, the B hospital 704b, and the E clinic 704e are selected by one patient. Then, second selection information indicating that medical terminals placed at the A hospital 704a, the B hospital 704b, and the E clinic 704e are applied as the "providing destinations" is inputted. Then, the provision agreement information including the first and second selection information is transmitted from the patient terminal 110.

On the provision of the shared chart, the processing in the step S22, the step S25, the step S26, the step S27, and the step S28 in FIG. 6 is performed by the following operations.

Incidentally, medical server apparatuses are individually placed at the medical-related facilities shown in FIG. 8A and in FIG. 8B.

In the processing in the step S22, the shared server apparatus 160 confirms the first and second selection information as well as the provision agreement information.

Then, in the processing in the step S25 and the step S26, the shared server apparatus 160 obtains the electronic charts provided from the medical terminals indicated by the first selection information, i.e. the electronic charts managed or maintained on the medical server apparatuses corresponding to the A hospital 704a, the B hospital 704b, the D clinic 704d, and the E clinic 704e shown in FIG. 8A.

Then, in the processing in the step S27, the shared server apparatus 160 makes the shared chart at least partially including the electronic charts provided from the medical server apparatuses corresponding to the A hospital 704a, the B hospital 704b, the D clinic 704d, and the E clinic 704e.

Then, in the processing in the step S28, the shared server apparatus 160 transmits the made shared chart to any one of the medical terminals indicated by the second selection information, i.e. the medical terminals placed at the A hospital 704a, the B hospital 704b, and the E clinic 704e shown in FIG. 8B.

Thus, in the fourth embodiment, the electronic chart managed or maintained at the C clinic 704c which is not regarded to be applied as the patient data source is not included in the shared chart, and the shared chart is not provided for the C clinic 704c and the D clinic 704d which are not regarded to be applied as the providing destinations of the shared chart.

Therefore, according to the fourth embodiment, by virtue of the first selection information included in the provision agreement information, the patient A can agree about a role as the patient data source of the shared chart, not for all medical-related facilities without exception, but for each medical-related facility under the control by the shared server apparatus 160. Moreover, by virtue of the second selection information included in the provision agreement information, the patient A can agree about a role as the providing destination of the shared chart, not for all medical-related facilities without exception, but for each medical-related facility.

Incidentally, this embodiment may be constructed such that the second selection information indicates a medical terminal that is selected to have the application as the providing destination of the shared chart, for each medical terminal that is selected to have the application as the patient data source of the shared chart on the basis of the first selection information. Alternatively, this embodiment may be constructed such that the first selection information indicates a medical terminal that is selected to have the application as the patient data source of the shared chart, for each medical terminal that is selected to have the application of the shared chart as the providing destination on the basis of the second selection information.

In any cases, under the control by the shared server apparatus 160, it is possible to share the shared chart having different contents among different medical-related facilities, for each type of the patient data source or for each medical-related facility.

Suppose that the above-explained fourth embodiment is applied to the second embodiment. In the processing in the step S27, the shared server apparatus 160 makes the shared chart which at least partially includes the electronic charts provided from the medical server apparatuses corresponding to the A hospital 704a, the B hospital 704b, the D clinic 704d, and the E clinic 704e and which does not include the electronic chart provided from the C clinic 704c. Therefore, even if the fourth embodiment is applied to the second embodiment, as is in the fourth embodiment described above, by virtue of the first selection information included in the provision agreement information, the patient A can agree about a role as the patient data source of the shared chart, not for all medical-related facilities without exception, but for each medical-related facility. Moreover, by virtue of the second selection information included in the provision agreement information, the patient A can agree about a role as the providing destination of the shared chart, not for all medical-related facilities without exception, but for each medical-related facility.

<5: Fifth Embodiment>

Figure 9:
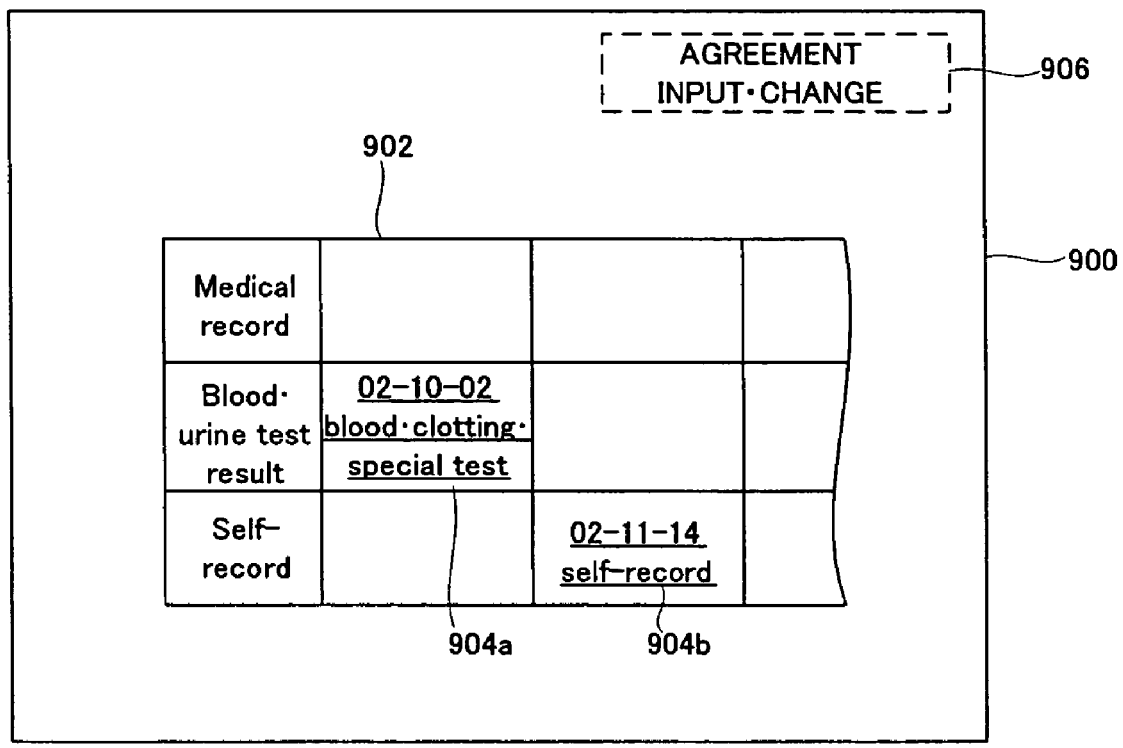
FIG. 9 is a schematic diagram showing one example of a display screen of a patient participatory chart.
Figure 10:
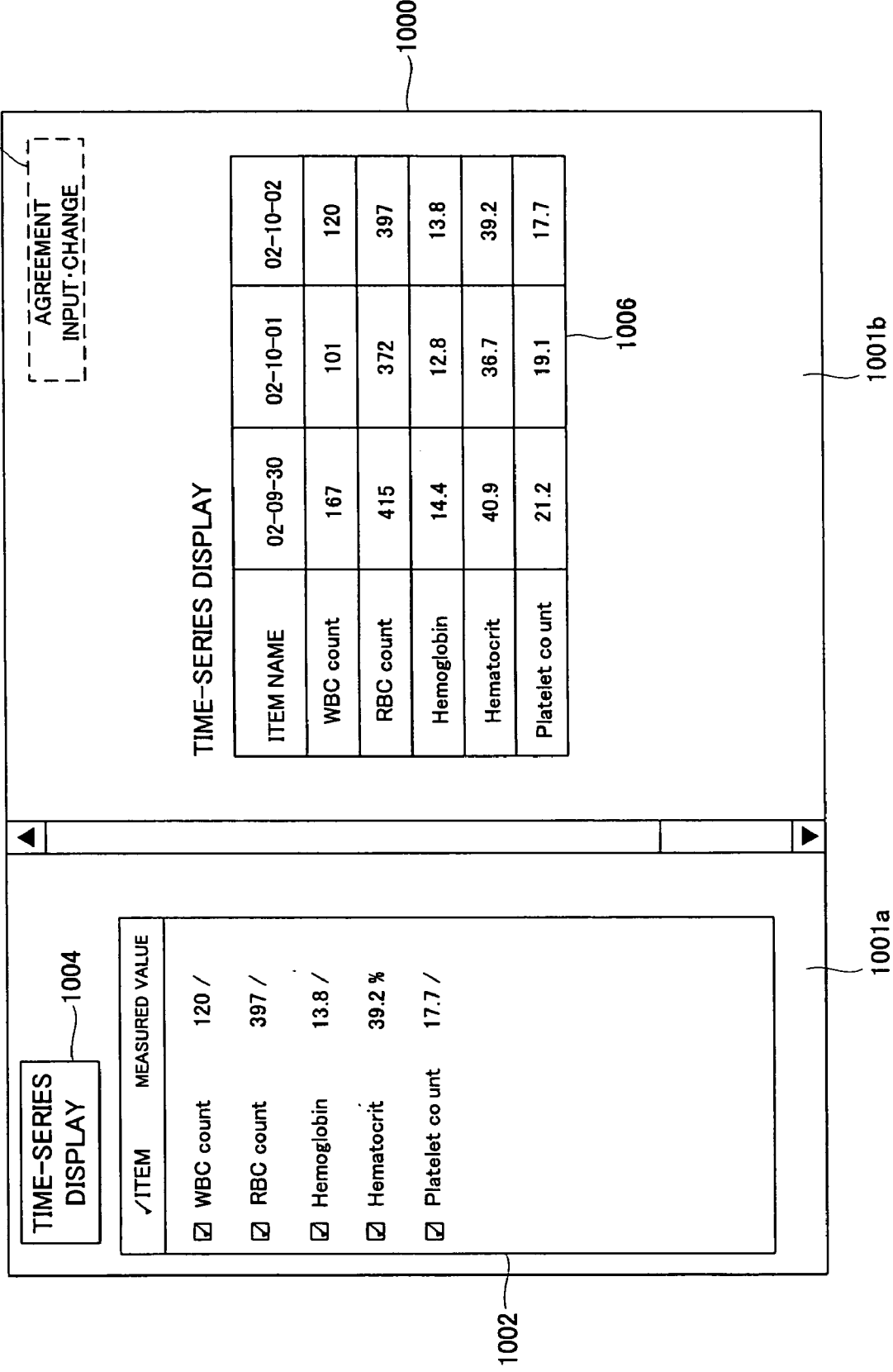
FIG. 10 is a schematic diagram showing another example of the display screen of the patient participatory chart.

Next, the fifth embodiment related to the medical information system of the present invention will be explained. Its detailed operations related to the provision of the patient participatory chart are different from those in the first to fourth embodiments. The operations thereof will be explained with reference to FIG. 2, FIG. 4, FIG. 5, FIG. 9, and FIG. 10. FIG. 9 shows one example of a display screen of a patient participatory chart. FIG. 10 shows another example of the display screen of a patient participatory chart.

In the fifth embodiment, the electronic charts are provided for the patient server apparatus 170 from the core hospital server apparatus 150a and the clinic server apparatus 150b in FIG. 1. In the meanwhile, the shared chart is provided for the patient server apparatus 170 from the shared server apparatus 160.

On the provision of the patient participatory chart, the processing in the step S14 and the step S16 in FIG. 4 is performed by the following operations.

In the processing in the step S14, the patient server apparatus 170 obtains the electronic charts and the shared chart which are related to the identified patient identification information and password, makes the patient participatory chart at least partially including the obtained electronic charts and shared chart, and provides them for the patient terminal 110.

In the processing in the step S14, the electronic charts and the shared chart are obtained as follows. The patient server apparatus 170 requests the core hospital server apparatus 150a and the clinic server apparatus 150b to provide the electronic charts related to the identified patient identification information and password. The patient server apparatus 170 also requests the shared server apparatus 160 to provide the shared chart related to the identified patient identification information and password.

When receiving request signals for the electronic charts, the core hospital server apparatus 150a and the clinic server apparatus 150b provide the patient server apparatus 170 with the electronic charts corresponding to the request signals. When receiving a request signal, the shared server apparatus 160 also provides the patient server apparatus with the shared chart corresponding to the request signal.

Then, in the processing in the step S16, a display screen 900 of the patient participatory chart is displayed as shown in FIG. 9, for example. The display screen 900 displays an implementation record related to a medical record, a blood and urine test result, and a self-record on a table 902 on which the various records are sorted. The patient data related to the medical record and the blood and urine test result is made or obtained on the first medical terminal 130a and the second medical terminal 130*b*. The patient data related to the self-record is made on the patient terminal 110.

On the table 902 on the display screen 900, the dates (year-month-date) when the medical record, the blood and urine test result, and the self-record are individually performed and the content thereof are displayed. More specifically, with respect to the blood and urine test result, its implementation date "Feb. 10, 2002" is displayed, as well as "blood•clotting•special test" indicating the content thereof. Even as for the self-record, its implementation date "Feb. 11, 2014" is displayed, as well as "self-record" indicating the content thereof.

The implementation record displayed on the table 902 is regarded as first mark information. Namely, the implementation date (year-month-date) and the content of the test are displayed as first marks 904*a* and 904*b*. The patient A can refer to detailed information related to the implementation record by clicking on the first mark 904*a* or 904*n* with a mouse, for example.

More specifically, the patient A can refer to a display screen 1000 shown in FIG. 10 by clicking on the implementation record 904*a* related to the displayed blood and urinary test. Moreover, the patient A can click on the implementation record 904*b* related to the displayed self-record to display another reference screen, and the patient A can refer to the patient data related to the patient self-supervision record made on the input screen 500*b* shown in FIG. 5B, as the detailed content of the implementation record of interest.

When the patient A clicks on the first mark 904*a* on the display screen 900, the display screen 1000 is displayed on the patient participatory chart. When the display screen 1000 is displayed, a table 1002 for indicating the test result of the blood•clotting•special test for each item is displayed on a screen portion 1001*a*. On this table 1002, a value for indicating the test result is displayed for each item. At the upper left of the table 1002, the first mark information for displaying time-series values for each item displayed on the table 1002 is displayed as a first mark 1004.

Then, by the patient A clicking on the first mark 1004 with a mouse, for example, a table 1006 for displaying the time-series values for each item displayed on the table 1002 is displayed on a screen portion 1001*b*. Incidentally, as shown in FIG. 10, it is possible to display a scroll bar for scrolling the screen portion 1001*b* to refer, for example.

On the patient terminal 110, second mark information indicating to call up the input screen 300 shown in FIG. 3 is displayed as second marks 906 and 1008 on the display screen 900 shown in FIG. 9 and on the display screen 1000 shown in FIG. 10.

When the patient A clicks on the second mark 906 or 1008 with a mouse, for example, the input screen 300 shown in FIG. 3 is displayed. Then, in the fifth embodiment, after the input screen 300 is displayed, at least one of the provision agreement information and the announcement agreement information can be inputted or changed in the same procedure as the processing in the step S2 shown in FIG. 2.

When the provision agreement information is inputted or changed, the inputted or changed provision agreement information is maintained on the shared server apparatus 160 in the same procedure as the processing in the step S4 shown in FIG. 2. When the announcement agreement information is inputted or changed, the inputted or changed announcement agreement information is maintained on the patient server apparatus 170 in the same procedure as the processing in the step S4 shown in FIG. 2.

As described above, in the fifth embodiment, the electronic charts and the shared chart are at least partially referred on a reference screen in a predetermined format from the display screen 900 or 1000 of the patient participatory chart on the patient terminal 110 side. Shortly before or after, or at the same time of the display of this reference screen, at least one of the provision agreement information and the announcement agreement information is inputted or changed. After confirming the content of the electronic charts and the content of the shared chart made by the present time point, the patient A can perform the input operation for the agreement about the provision of the shared chart and the agreement about the medical announcement.

Incidentally, what can be referred on the patient terminal 110 side may be all of the electronic charts or all of the shared chart; however, information, such as "patient attribute information", "shared chart registration information", "patient participatory chart registration information", "patient will confirmation information", and "patient health card information", is useful for the patient A in practice. Moreover, in the fifth embodiment, the display may be performed to show the provision of what type of information and for which medical-related facility the patient A agrees about. For example, a list of clinics which are selected to be referable may be displayed. Furthermore, in addition to or in place of controlling, for each medical-related facility, the medical-related facility where the shared chart can be referred, it can be controlled selectively for a predetermined type among data.

In the fifth embodiment, it is possible to easily refer to one portion of the electronic charts and the shared chart on the reference screen displayed by specifying the first mark information displayed on the display screen 900 or 1000 of the patient participatory chart on the patient terminal 110. This makes it possible to easily perform the input operation of the provision agreement information and the announcement agreement information.

In the fifth embodiment, it is possible to perform the input operation of the provision agreement information and the announcement agreement information quickly and easily, by specifying the second mark information displayed on the display screen 900 or 1000 of the patient participatory chart and by calling up the input screen 300 shown in FIG. 3, during the confirmation of the reference screen on which one portion of the electronic charts and the shared chart is displayed or after the conformation without any delay.

<6: Sixth Embodiment>

Figure 11:
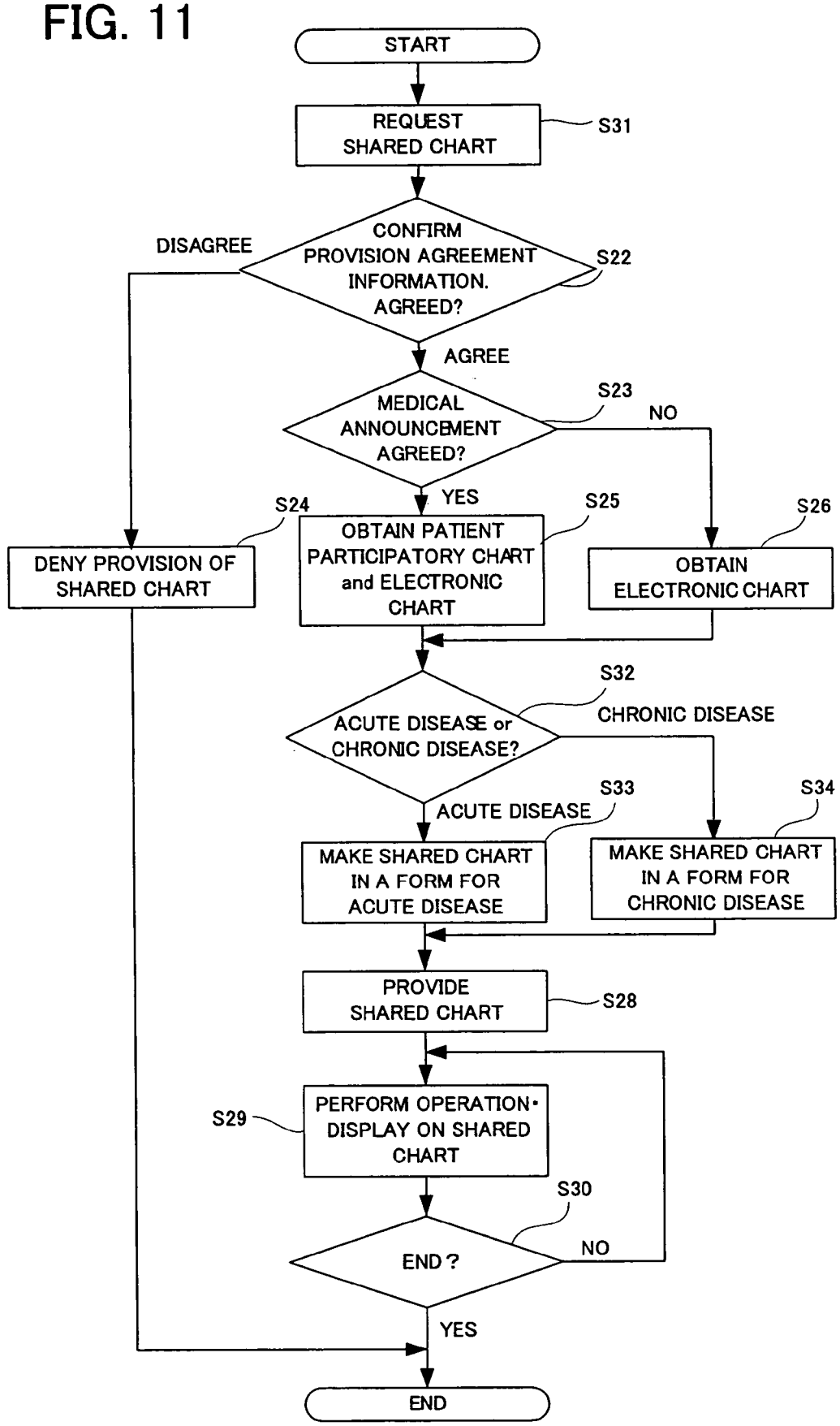
FIG. 11 is a flowchart showing one operation of a medical information system in a sixth embodiment.

Next, the sixth embodiment related to the medical information system of the present invention will be explained. Its detailed operations related to the provision of the shared chart are different from those in the first to fifth embodiments. The operations thereof will be explained with reference to FIG. 11. FIG. 11 shows the operation related to the provision of the shared chart in the sixth embodiment. Incidentally, the case of providing the shared chart for the first medical terminal 130*a* will be explained hereinafter, but the same is true in the case of providing the shared chart for the second medical terminal 130*b* as in the case for the first medical terminal 130*a*.

Firstly, the first medical terminal 130*a* requests the shared server apparatus 160 to provide the shared chart by keyboard operation or the like. In this case, a request signal indicating a request for the use of the shared chart with a distinction between an acute disease and a chronic disease is transmitted from the first medical terminal 130a to the shared server apparatus 160 through the communication network (step S31).

Then, as in the first to fifth embodiments, the operations between the step S22 and the step S26 are performed.

Then, the shared server apparatus 160 confirms for which disease the shared chart is requested, the acute diseases or the chronic disease, by the received request signal (step S32).

When the received request signal requests for the shared chart about the acute disease (the step S32: acute disease), the shared server apparatus 160 makes the shared chart in a preset form for the acute disease, which preferentially indicates medication records and a previous history of the patient A related to the shared chart of interest, out of the patient data included in the shared chart maintained on the shared server apparatus 160 (step S33).

When the received request signal requests for the shared chart about the chronic disease (the step S32: chronic disease), the shared server apparatus 160 makes the shared chart in a preset form for the chronic disease, which preferentially indicates a disease name and medication records of the patient A related to the shared chart of interest, out of the patient data included in the shared chart maintained on the shared server apparatus 160 (step S34).

Then, as in the first to fifth embodiments, after the operations in the step S28 to the step S30 are performed, a series of operations related to the provision of the shared chart is ended.

According to the sixth embodiment, it is possible to refer to the shared chart which includes information about the medication records and the previous history (allergy or the like) for implementing appropriate prescriptions and tests, which are more important about the acute disease from the medical viewpoint. Therefore, it is possible to provide high quality medication for the patient who has the acute disease.

On the other hand, it is possible to refer to the shared chart which includes information about a disease name, e.g. diabetes, and medication records, which are more important about the chronic disease from the medical viewpoint. Therefore, it is possible to provide high quality medication for the patient who has the chronic disease.

<7: Seventh Embodiment>

Next, the seventh embodiment related to the medical information system of the present invention will be explained with reference to FIG. 1.

In FIG. 1, any one of the first medical terminal 140a and the second medical terminal 140b is constructed to display a screen for providing medical care, with the screen being switched from the display of the electronic charts or the shared chart. By constituting in this manner, the first medical terminal 140a and the second medical terminal 140b allow "email medical care" through the communication network with the patient terminal 110 by using the screen for providing medical care.

The patient terminal 110 is constructed to display a screen for receiving medical care, with the screen being switched from the display of the patient participatory chart. By constituting in this manner, the patient terminal 110 allows the reception of the email medical care through communication network with any one of the first medical terminal 140a and the second medical terminal 140b by using the screen for receiving medical care.

The core hospital server apparatus 150a reflects, in the electronic charts, the patient data newly inputted through the screen for providing medical care on the first medical terminal 140. The clinic server apparatus 150b also reflects, in the electronic charts, the patient data newly inputted through the screen for providing medical care, as with the core hospital server apparatus 150a.

In addition, the patient server apparatus 170 reflects, in the patient participatory chart, the patient data newly inputted through the screen for receiving medical care on the patient terminal 110.

Thus, according to the seventh embodiment, it allows the email medical care (including the first consultation and a repeat consultation). Then, the patient data newly inputted through the screen for providing medical care and the screen for receiving medical care during the email medical care in this manner is reflected in the electronic charts and the patient participatory chart. Consequently, the electronic charts, the shared chart, and further the patient participatory chart can be updated without any delay.

Incidentally, in place of or in addition to this type of email medical care, this embodiment may be constructed to perform telephone medical care (including the first consultation and a repeat consultation) through the communication network. For example, this embodiment may be constructed such that the patient terminal 110 sends a call for a repeat consultation by a phone which is at a medical-related facility corresponding to any one of the first medical terminal 140a and the second medical terminal 140b, with the patient participatory chart being displayed.

Alternatively, the embodiment may be constructed such that the patient terminal 110 displays a repeat consultation reservation screen for reserving a repeat consultation at the medical-related facility corresponding to any one of the first medical terminal 140a and the second medical terminal 140b or at another medical-related facility, with the screen being switched from the display of the patient participatory chart. Moreover, the patient terminal 110 may be also constructed to perform the repeat consultation reservation on the displayed repeat consultation reservation screen.

<8: Eighth Embodiment>

Figure 12:
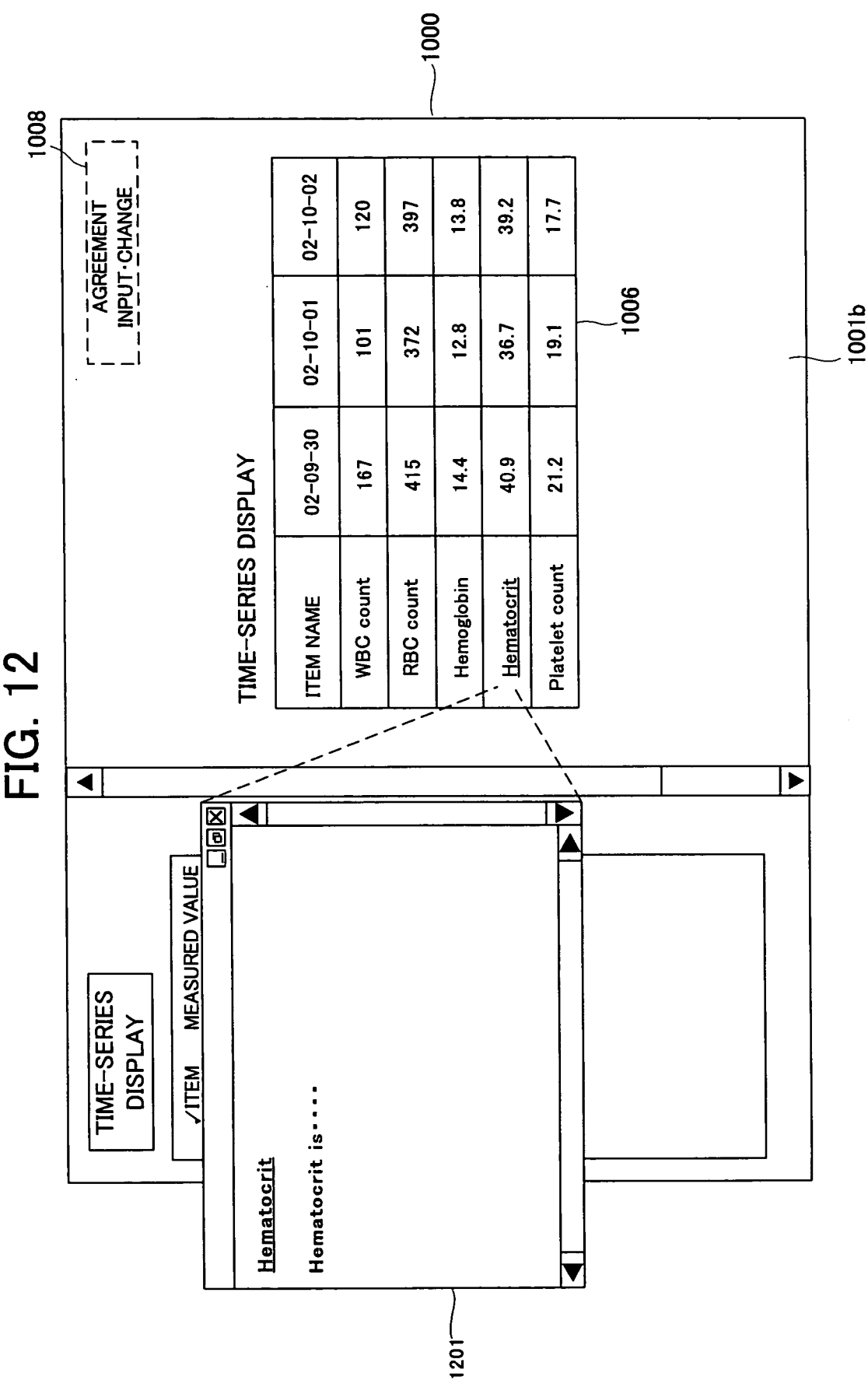
FIG. 12 is a schematic diagram showing one example of a screen in the case of searching for terms.

Next, the eighth embodiment related to the medical information system of the present invention will be explained with reference to FIG. 1 to FIG. 12. FIG. 12 is a schematic diagram showing one example of a screen in the case of searching for terms on the display screen shown in FIG. 10.

When unknown or unused terms are displayed on the display screen of the patient participatory chart displayed on the patient terminal 110, the patient A can search for the terms in the following procedures.

On the patient terminal 110, "hematocrit" is specified as a search object by cursor operation with a mouse and a keyboard or by similar operation, out of terms displayed on the screen portion 1001b on the display screen 1000 shown in FIG. 10, for example.

Then, the patient server apparatus 170 calls up a site, which is operated by the patient server apparatus 170 or another server apparatus, through the communication network in order to search for the "hematocrit" specified as the search object on the patient terminal 110. Then the patient server apparatus 170 provides the called site for the patient terminal 110 through the communication network.

On the patient terminal 110, a browser screen of the called site is displayed by screen switching and window displaying. FIG. 12 shows a window 1201 for displaying information indicating the meaning of the searched "hematocrit" is displayed on the display screen 1000.

Therefore, according to the eighth embodiment, the patient A can simply and quickly search for various medical terms displayed on the display screen of the patient participatory chart, which has the unique structure of the present invention and the effects thereof as explained in the above-described various embodiments, by using the exclusive site for searching, which allows the patient A to understand the meaning easily.

Moreover, not only by linking the exclusive site for searching as shown in FIG. 12 but also by providing, for the patient terminal 110, information which more directly indicates the term specified as the search object on the patient terminal 110, the patient A can search for this term extremely quickly by a simple operation and can understand the meaning quickly.

<9: Modified Example>

Figure 13:
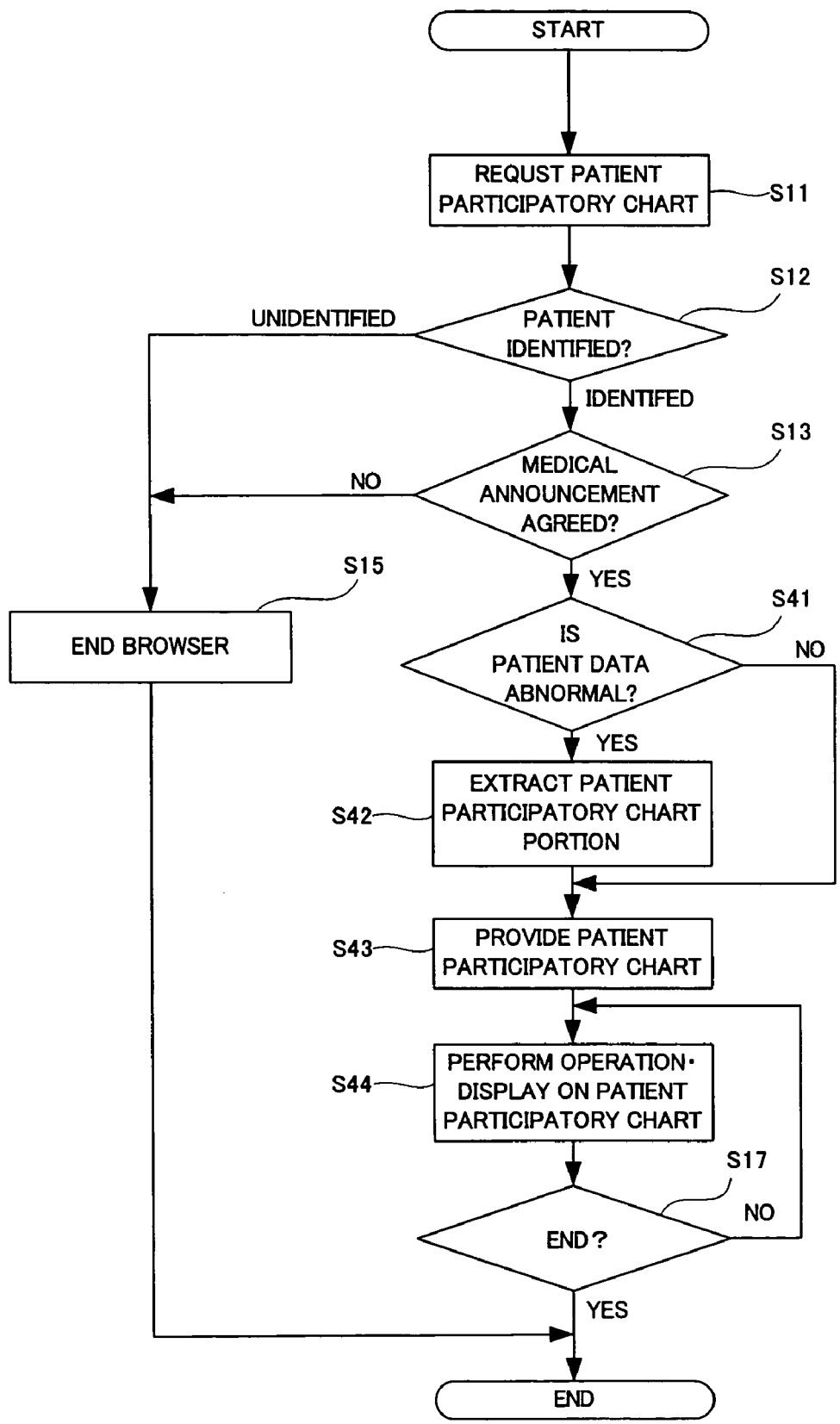
FIG. 13 is a flowchart showing one operation related to a modification example.

The modified example of the medical information system in the above-explained first to eighth embodiments will be explained with reference to FIG. 1, FIG. 4, and FIG. 13. FIG. 13 shows the operations related to the provision of the patient participatory chart in this modified example.

Firstly, in FIG. 1, the example may be constructed such that the patient terminal 110 can refer to history information indicating a history of the use of the patient participatory chart, on the patient participatory chart. The example may be constructed such that the first and second medical terminals 130a and 130b do not to refer to the history information on the electronic charts or the shared chart.

By constituting in this manner, it is absolutely possible to guarantee even the right to know the patient data regarding the patient A himself, the right to know the history of the use of the electronic charts, the patient participatory chart, or the shared chart, or the right to keep the history of the use from a third person, all of which are owned on the patient side.

Moreover, the example may be constructed such that the patient terminal 110 cannot change a patient data portion related to items which are different from the predetermined items that can be inputted by one patient and which are inputted through the core hospital server apparatus 150a or the clinic server apparatus 150b. Also, the example may be constructed such that the patient terminal 110 can add correction demand information indicating a demand of correction for the patient data portion if desired.

By constituting in this manner, it is possible to guarantee a copyright owned on the core hospital 140a and the clinic 140b side which make the patient data portion. At the same time, when mistakes, errors, or the like are found, the correction demand information indicating a demand of correction can be added from the patient terminal 110 side to the patient data portion. Therefore, it is possible to guarantee the right to demand the correction of information about the patient A's own charts owned on the patient A side.

Furthermore, the example may be constructed such that particular matter information which is not to be written in the patient participatory chart can be inputted from any one of the first and second medical terminals 130a and 130b. In the operations related to the provision of the patient participatory chart shown in FIG. 4, when one patient, the patient A, makes agreement based on the announcement agreement information (step S13: YES), the patient server apparatus 170 provides the patient participatory chart in a form of removing the particular matter information for the patient terminal 110 in the processing in the step S14.

Thus, with respect to the particular matter information which can be inputted from the first and second medical terminals 130a and 130b and which is not to be written in the patient participatory chart, even when the patient A agrees about the announcement on the basis of the announcement agreement information, it is not included in patient participatory chart provided from the patient server apparatus 170. Namely, it is possible to keep this particular matter information from the patient A. As the "particular matter information", the following is conceivable: (i) "paperwork" and "work communication" which are information about work in a hospital and which does not have a direct connection or any connection with the medical state, treatment, and medical care of the patient A, (ii) "nurse's record" which is remotely related to the medical state, treatment, and medical care of the patient A in spite of large information amounts in the work, and the like. The "particular matter information" includes information which increases the amount of data when included in the patient participatory chart, thereby to make the patient participatory chart hard to see or to decrease its usability. Alternatively, the "particular matter information" includes information which seems to be not good to be informed of the patient A in view of the nature of the information, such as "information about clinical judgment of mental illness or the like". By removing these information from the patient participatory chart, it is possible to make the patient participatory chart easier to refer to, and also it is possible to prevent negative effects caused by showing the patient participatory chart to the patient A.

In addition, the example may be constructed such that the patient server apparatus 170 judge whether or not the patient data constituting the patient participatory chart is abnormal in accordance with a predetermined standard on the provision of the patient participatory chart.

When the example is constructed as described above, the provision of the patient participatory chart is performed by the patient server apparatus 170 as follows. Incidentally, the explanation below is focused only on the different points from the first to eighth embodiments.

The patient server apparatus 170 judges whether or not the patient data constituting the patient participatory chart is abnormal in accordance with the predetermined standard (step S41). When it is judged that the patient data constituting the patient participatory chart is abnormal (the step S41: YES), the patient server apparatus 170 extracts the abnormal patient data and a patient participatory chart portion including the patient data related to this abnormal patient data (step S42).

Then, the patient server apparatus 170 provides the extracted patient participatory chart portion for the patient terminal 110 (step S43). When it is judged that the patient data constituting the patient participatory chart is not abnormal (the step S41: NO), the patient participatory chart is provided in the same way as those of the first to eighth embodiments (the step S43).

Then, the patient terminal 110 performs an operation on the patient participatory chart (step S44), which allows the output of the provided patient participatory chart portion in a predetermined format.

Not only the patient participatory chart is displayed without exception, but also the abnormal patient data and the patient participatory chart portion including the patient data related to this abnormal patient data are displayed and outputted, or printed and outputted, on the patient terminal 110 side. Thus, it is possible to refer to the patient participatory chart with a focus on a part which has a high possibility to have problems on the patient A's own health.

Incidentally, the example may be constructed such that items with abnormal values, display focusing on the (examination) date or the like, time-series display are also displayed simultaneously, in addition to the display of the electronic charts in typical various formats.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2003-305153 filed on Aug. 28, 2003 including the specification, claims, drawings and summary is incorporated herein by reference in its entirety.

What is claimed is:

1. A medical information system comprising:
    a medical server apparatus for providing an electronic chart, which includes patient data related to medical care of one patient made or obtained through each of a plurality of medical terminals placed at a plurality of medical-related facilities in one area, for the plurality of the medical terminals for each of the medical-related facilities;
    a patient server apparatus capable of providing a patient participatory chart, which at least partially includes the electronic chart provided from said medical server apparatus and which includes patient data related to predetermined items made or obtained through a patient terminal operated by the one patient, for the patient terminal; and
    a shared server apparatus capable of providing a shared chart, which at least partially includes the electronic chart provided from said medical server apparatus and the patient participatory chart provided from said patient server apparatus and which is integrally made for the one patient, for at least one of the plurality of medical terminals,
    wherein
    said medical server apparatus, said patient server apparatus, said shared server apparatus, the plurality of medical terminals, and the patient terminal are included in a communication network,
    at least one of the plurality of medical terminals and the patient terminal is capable of inputting (i) announcement agreement information indicating agreement of the one patient about medical announcement and (ii) provision agreement information indicating agreement of the one patient about provision of the shared chart, and is capable of transmitting at least one of the inputted announcement agreement information and provision agreement information through the communication network,
    said patient server apparatus (i) provides the patient participatory chart for the patient terminal in case that the one patient agrees about the medical announcement and (ii) does not provide the patient participatory chart for the patient terminal in case that the one patient disagrees about the medical announcement, on the basis of the announcement agreement information transmitted through the communication network, and
    said shared server apparatus (i) provides, in case that the one patient agrees about the provision on the basis of the provision agreement information transmitted through the communication network: (i-a) the shared chart, which includes the patient data inputted through the patient terminal so as to be one portion of the patient participatory chart, for at least one of the plurality of medical terminals if the one patient agrees about the medical announcement ; and (i-b) the shared chart not-including the patient data inputted through the patient terminal so as to be one portion of the patient participatory chart for at least one of the plurality of medical terminals if the one patient disagrees about the medical announcement, and (ii) does not provide the shared chart for any of the plurality of medical terminals in case that the one patient disagrees about the provision, on the basis of the provision agreement information transmitted through the communication network.

2. The medical information system according to claim 1, wherein
    said medical server apparatus (i) provides the electronic chart, which is about the one patient made or obtained on said medical server apparatus, for said shared server apparatus in case that the one patient agrees about the provision and (ii) does not provide the electronic chart, which is about the one patient made or obtained on said medical server apparatus, for said shared server apparatus in case that the one patient disagrees about the provision, on the basis of the provision agreement information, and
    said shared server apparatus at least partially incorporates the electronic chart provided from said medical server apparatus to thereby make the shared chart.

3. The medical information system according to claim 1, wherein
    said medical server apparatus provides the electronic chart, which is about the one patient made or obtained on said medical server apparatus, for said shared server apparatus, and
    said shared apparatus (i) at least partially incorporates the electronic chart provided from said medical server apparatus to thereby make the shared chart in case that the one patient agrees about the provision and (ii) does not make the shared chart when the one patient disagrees about the provision, on the basis of the provision agreement information.

4. The medical information system according to claim 1, wherein
    the patient terminal can transmit, through the communication network, chart request information indicating a request for the provision of the patient participatory chart as well as patient identification information indicating identification of the one patient and a password corresponding to the patient identification information, and
    said patient server apparatus provides the patient participatory chart for the patient terminal in case that the one patient agrees about the medical announcement and that the one patient can be identified by verifying the patient identification information and password transmitted through the communication network.

5. The medical information system according to claim 1, wherein
    the patient terminal is capable of inputting or changing and transmitting the provision agreement information as well as patient identification information indicating identification of the one patient and a password corresponding to the patient identification information, and
    said shared server apparatus takes the inputted or changed provision agreement information to be valid in case that the one patient can be identified by verifying the patient identification information and password transmitted through the communication network.

6. The medical information system according to claim 1, wherein the patient terminal is capable of referring to history information indicating a history of use of the patient participatory chart on the patient participatory chart, and each of the medical terminals is not capable of referring to the history information on the electronic chart or the shared chart.

7. The medical information system according to claim 1, wherein the provision agreement information includes selection information indicating a medical terminal or terminals selected to have application of the shared chart out of the plurality of medical terminals, said shared server apparatus makes the shared chart so as to at least partially include the electronic chart provided from the medical terminal or terminals selected to have the application of the shared chart and so as not to include the electronic chart provided from a medical terminal regarded not to have the application of the shared chart, on the basis of the selection information, and said shared server apparatus provides the made shared chart for the medical terminal or terminals selected to have the application of the shared chart and does not provide the made shared chart for the medical terminal regarded not to have the application of the shared chart, on the basis of the selection information.

8. The medical information system according to claim 1, wherein the provision agreement information includes first selection information indicating a medical terminal or terminals selected to have application as a patient data source of the shared chart out of the plurality of medical terminals and second selection information indicating a medical terminal or terminals selected to have application as a providing destination of the shared chart, said shared server apparatus makes the shared chart so as to at least partially include the electronic chart provided from the medical terminal or terminals selected to have the application as the patient data source of the shared chart and so as not to include the electronic chart provided from a medical terminal regarded not to have the application as the patient data source of the shared chart, on the basis of the first selection information, and said shared server apparatus provides the made shared chart for the medical terminal or terminals selected to have the application as the providing destination of the shared chart and does not provide the made shared chart for a medical terminal regarded not to have the application as the providing destination of the shared chart, on the basis of the second selection information.

9. The medical information system according to claim 1, wherein said medical server apparatus and said shared server apparatus at least partially provide the electronic chart and the shared chart for the patient terminal, the patient terminal is capable of at least partially referring to the electronic chart provided from said medical server apparatus and the shared chart provided from said shared server apparatus in a predetermined format, from a display screen of the patient participatory chart, and is capable of inputting or changing at least one of the provision agreement information and the announcement agreement information, shortly before or after, or at the same time of the display of a reference screen in the predetermined format, said shared server apparatus maintains the inputted or changed provision agreement information, and makes and provides the shared chart in accordance with the provided provision agreement information, and said patient server apparatus maintains the inputted or changed announcement agreement information, and makes and provides the patient participatory chart in accordance with the provided announcement agreement information.

10. The medical information system according to claim 9, wherein the patient terminal can display first mark information indicating to call up the reference screen in the predetermined format on the display screen of the patient participatory chart, and can display the reference screen in the predetermined format by specifying the displayed first mark information.

11. The medical information system according to claim 9, wherein the patient terminal can display second mark information indicating to call up an agreement input screen of at least one of the announcement agreement information and the provision agreement information on the reference screen in the predetermined format, can call up the agreement input screen by specifying the displayed second mark information, and is capable of inputting at least one of the announcement agreement information and the provision agreement information on the called agreement input screen.

12. The medical information system according to claim 1, wherein at least one of the plurality of medical terminals can transmit chart request information indicating a request for use of the shared chart with a distinction between an acute disease and a chronic disease related to the one patient, to said shared server apparatus through the communication network, said shared server apparatus transmits the shared chart in a preset form for the acute disease, which preferentially indicates medication records and a previous history of the one patient, out of the patient data included in the shared chart maintained on the shared server apparatus, to the medical terminal which transmits the chart request information, in case that the shared chart about the acute disease is requested, and said shared server apparatus transmits the shared chart in a preset form for the chronic disease, which preferentially indicates a disease name and medication records of the one patient, out of the patient data included in the shared chart maintained on the shared server apparatus, to the medical terminal which transmits the chart request information, in case that the shared chart about the chronic disease is requested.

13. The medical information system according to claim 1, wherein at least one of the plurality of medical terminals can display a screen for providing medical care, which is intended to perform email medical care through the communication network with the patient terminal, with the screen for providing medical care being switched from display of the electronic chart or the shared chart, the patient terminal can display a screen for receiving medical care, which is intended to receive the email medical care through the communication network with at least one of the medical terminals, with the screen for receiving medical care being switched from display of the patient participatory chart, and said medical server apparatus and said patient server apparatus reflect patient data newly inputted through the screen for providing medical care and the screen for receiving medical care to the electronic chart and the patient participatory chart, respectively.

14. The medical information system according to claim 1, wherein the patient terminal is capable of specifying, as a search object, a term described on the patient participatory chart by an input operation of a predetermined type, on a display screen of the patient participatory chart provided from said patient server apparatus, and said patient server apparatus further calls up a site, which is operated by said patient server apparatus or another server apparatus, for searching for the term through the communication network in case that the term is specified as the search object, and provides the site to the patient terminal.

15. A medical information system comprising:

a medical server apparatus for providing an electronic chart, which includes patient data related to medical care of one patient made or obtained through each of a plurality of medical terminals placed at a plurality of medical-related facilities in one area, for the plurality of the medical terminals for each of the medical-related facilities; and a patient server apparatus capable of providing a patient participatory chart, which at least partially includes the electronic chart provided from said medical server apparatus and which includes patient data related to predetermined items made or obtained through a patient terminal operated by the one patient, for the patient terminal, wherein said medical server apparatus, said patient server apparatus, the plurality of medical terminals, and the patient terminal are included in a communication network, at least one of the plurality of medical terminals and the patient terminal is capable of inputting announcement agreement information indicating agreement of the one patient about medical announcement, and is capable of transmitting the inputted announcement agreement information through the communication network, said patient server apparatus (i) provides the patient participatory chart for the patient terminal in case that the one patient agrees about the medical announcement and (ii) does not provide the patient participatory chart for the patient terminal in case that the one patient disagrees about the medical announcement, on the basis of the announcement agreement information transmitted through the communication network, the patient terminal is capable of specifying, as a search object, a term described on the patient participatory chart by an input operation of a predetermined type, on a display screen of the patient participatory chart provided from said patient server apparatus, and said patient server apparatus further calls up a site, which is operated by said patient server apparatus or another server apparatus, for searching for the term through the communication network in case that the term is specified as the search object, and provides the site for the patient terminal.

16. The medical information system according to claim 15, wherein said patient server apparatus provides the site for the patient terminal while showing information indicating the meaning of the specified term.

17. The medical information system according to claim 1, wherein the patient terminal is capable of inputting or changing and transmitting the announcement agreement information as well as patient identification information indicating identification of the one patient and a password corresponding to the patient identification information, and said patient server apparatus takes the inputted or changed announcement agreement information to be valid in case that the one patient can be identified by verifying the patient identification information and password transmitted through the communication network.

18. The medical information system according to claim 1, wherein the patient terminal cannot change a patient data portion related to items, which are different from the predetermined items that can be inputted by the one patient and which are inputted through said medical server apparatus, and can add correction demand information indicating a demand of correction with respect to the patient data portion if desired.

19. The medical information system according to claim 1, wherein particular matter information which is not to be written in the patient participatory chart can be inputted from at least one of the plurality of medical terminals, and said patient server apparatus provides the patient participatory chart in a form of removing the particular matter information for the patient terminal in case that the one patient agrees about the medical announcement on the basis of the provision agreement information.

20. The medical information system according to claim 1, wherein said patient server apparatus judges whether or not the patient data constituting the patient participatory chart is abnormal in accordance with a predetermined standard, extracts the abnormal patient data and a patient participatory chart portion including the patient data related to the abnormal patient datain case that it is judged as a judgment result that the patient datais abnormal, and provides the extracted patient participatory chart portion for the patient terminal, and the patient terminal can output the provided patient participatory chart portion in a predetermined format.

21. A computer program product in a computer-readable medium for tangibly embodying a program of instructions executable by a computer to make the computer function as a medical information system, said medical information system comprising:

a medical server apparatus for providing an electronic chart, which includes patient data related to medical care of one patient made or obtained through each of a plurality of medical terminals placed at a plurality of medical-related facilities in one area, for the plurality of the medical terminals for each of the medical-related facilities;

a patient server apparatus capable of providing a patient participatory chart, which at least partially includes the electronic chart provided from said medical server apparatus and which includes patient data related to predetermined items made or obtained through a patient terminal operated by the one patient, for the patient terminal; and a shared server apparatus capable of providing a shared chart, which at least partially includes the electronic chart provided from said medical server apparatus and the patient participatory chart provided from said patient server apparatus and which is integrally made for the one patient, for at least one of the plurality of medical terminals, wherein said medical server apparatus, said patient server apparatus, said shared server apparatus, the plurality of medical terminals, and the patient terminal are included in a communication network, at least one of the plurality of medical terminals and the patient terminal is capable of inputting (i) announcement agreement information indicating agreement of the one patient about medical announcement and (ii) provision agreement information indicating agreement of the one patient about provision of the shared chart, and is capable of transmitting at least one of the inputted announcement agreement information and provision agreement information through the communication network, said patient server apparatus (i) provides the patient participatory chart for the patient terminal in case that the one patient agrees about the medical announcement and (ii) does not provide the patient participatory chart for the patient terminal in case that the one patient disagrees about the medical announcement, on the basis of the announcement agreement information transmitted through the communication network, and said shared server apparatus (i) provides, in case that the one patient agrees about the provision on the basis of the provision agreement information transmitted through the communication network: (i-a)the shared chart, which includes the patient data inputted through the patient terminal so as to be one portion of the patient participatory chart, for at least one of the plurality of medical terminals if the one patient agrees about the medical announcement ; and (i-b) the shared chart not-including the patient data inputted through the patient terminal so as to be one portion of the patient participatory chart for at least one of the plurality of medical terminals if the one patient disagrees about the medical announcement, and (ii) does not provide the shared chart for any of the plurality of medical terminals in case that the one patient disagrees about the provision, on the basis of the provision agreement information transmitted through the communication network.

22. A computer program product in a computer-readable medium for tangibly embodying a program of instructions executable by a computer to make the computer function as a medical server apparatus, a patient server apparatus, or a shared server apparatus provided in a medical information system, said medical information system comprising:

said medical server apparatus for providing an electronic chart, which includes patient data related to medical care of one patient made or obtained through each of a plurality of medical terminals placed at a plurality of medical-related facilities in one area, for the plurality of the medical terminals for each of the medical-related facilities;

said patient server apparatus capable of providing a patient participatory chart, which at least partially includes the electronic chart provided from said medical server apparatus and which includes patient data related to predetermined items made or obtained through a patient terminal operated by the one patient, for the patient terminal; and said shared server apparatus capable of providing a shared chart, which at least partially includes the electronic chart provided from said medical server apparatus and the patient participatory chart provided from said patient server apparatus and which is integrally made for the one patient, for at least one of the plurality of medical terminals, wherein said medical server apparatus, said patient server apparatus, said shared server apparatus, the plurality of medical terminals, and the patient terminal are included in a communication network, at least one of the plurality of medical terminals and the patient terminal is capable of inputting (i) announcement agreement information indicating agreement of the one patient about medical announcement and (ii) provision agreement information indicating agreement of the one patient about provision of the shared chart, and is capable of transmitting at least one of the inputted announcement agreement information and provision agreement information through the communication network, said patient server apparatus (i) provides the patient participatory chart for the patient terminal in case that the one patient agrees about the medical announcement and (ii) does not provide the patient participatory chart for the patient terminal in case that the one patient disagrees about the medical announcement, on the basis of the announcement agreement information transmitted through the communication network, and said shared server apparatus (i) provides, in case that the one patient agrees about the provision on the basis of the provision agreement information transmitted through the communication network: (i-a)the shared chart, which includes the patient data inputted through the patient terminal so as to be one portion of the patient participatory chart, for at least one of the plurality of medical terminals if the one patient agrees about the medical announcement ; and (i-b) the shared chart not-including the patient data inputted through the patient terminal so as to be one portion of the patient participatory chart for at least one of the plurality of medical terminals if the one patient disagrees about the medical announcement, and (ii) does not provide the shared chart for any of the plurality of medical terminals in case that the one patient disagrees about the provision, on the basis of the provision agreement information transmitted through the communication network.

* * * * *